United States Patent
Göbel

(10) Patent No.: US 12,150,878 B2
(45) Date of Patent: Nov. 26, 2024

(54) APPLICATOR AND A METHOD FOR THE TRANSPYLORIC PLACEMENT OR REMOVAL OF A TRANSPYLORIC AND/OR A TRANSDUODENAL BYPASS DEVICE IN/FROM THE REGION OF THE PYLORUS OF A PATIENT

(71) Applicant: Trans-Duodenal Concepts GmbH, Waghäusel (DE)

(72) Inventor: Fred Göbel, Wilhelmsfeld (DE)

(73) Assignee: Trans-Duodenal Concepts GmbH (DE)

( * ) Notice: Subject to any disclaimer, the term of this patent is extended or adjusted under 35 U.S.C. 154(b) by 1048 days.

(21) Appl. No.: 16/875,053

(22) Filed: May 15, 2020

(65) Prior Publication Data
US 2020/0276040 A1   Sep. 3, 2020

Related U.S. Application Data

(63) Continuation-in-part of application No. 15/522,649, filed as application No. PCT/IB2015/002005 on Oct. 29, 2015, now Pat. No. 10,667,936.

(30) Foreign Application Priority Data

Oct. 29, 2014  (DE) .................. 10 2014 015 919.1

(51) Int. Cl.
*A61F 5/00* (2006.01)
*A61B 17/00* (2006.01)
(Continued)

(52) U.S. Cl.
CPC ............ *A61F 5/0089* (2013.01); *A61F 5/003* (2013.01); *A61F 5/0076* (2013.01);
(Continued)

(58) Field of Classification Search
CPC ............ A61F 5/0076; A61F 2250/0003; A61F 5/0003; A61F 5/0033; A61F 5/0089;
(Continued)

(56) References Cited

U.S. PATENT DOCUMENTS 5,820,584 A    10/1998  Crabb
9,295,574 B2 *  3/2016  Priplata ............. A61B 17/3468
(Continued)

FOREIGN PATENT DOCUMENTS

WO   WO 2008/106041    9/2008
WO   WO 2011/099940    8/2011
(Continued)

*Primary Examiner* — Leslie R Deak
(74) *Attorney, Agent, or Firm* — Pandiscio & Pandiscio

(57) ABSTRACT

An applicator (26) for a releasable coupling of a transpyloric and, if applicable, transduodenal bypass device (1) comprising a tubular, preferably radially collapsible and self-erecting transpyloric conducting element (4,7), which is or has to be placed in a patient in such a way that it penetrates the pylorus of the patient and is provided with a central conducting lumen comprising an upstream mouth to be placed antegrade of the pylorus and a downstream mouth to be placed retrograde of the pylorus, for (i) accepting the chyme from the stomach, for (ii) bypass-type conducting of the chyme through the pylorus and, if applicable, through the duodenum or a part of the duodenum, and for (iii) releasing the chyme in or beyond the duodenum of the patient, to an endoscope or a catheter having an elongated shaft (28), on the external surface of which the bypass device (1) can be placed and/or plugged in order to insert the bypass device (1) under direct guidance of the endoscope or catheter from the outside of the patient's body in an antegrade way through the upper digestive tract into the stomach, or to remove it in a retrograde way through the upper digestive tract, characterized in that the applicator (26) comprises a tubular coupling element (27), which is or can be slid onto the external
(Continued)

surface of the shaft (28) surrounding it, and which entirely or partially penetrates the central conducting lumen of the bypass device (1), thereby bridging a gap between the external surface of the shaft (28) and an internal surface of the central conducting lumen of the bypass device (1).

5 Claims, 10 Drawing Sheets

(51) Int. Cl.
*A61M 27/00* (2006.01)
*A61B 1/273* (2006.01)

(52) U.S. Cl.
CPC ......... *A61F 5/0079* (2013.01); *A61M 27/002* (2013.01); *A61B 1/2736* (2013.01); *A61B 2017/00292* (2013.01); *A61B 2017/00818* (2013.01)

(58) Field of Classification Search
CPC ................... A61F 5/003; A61F 5/0079; A61B 2017/00818; A61M 27/002
See application file for complete search history.

(56) References Cited

U.S. PATENT DOCUMENTS

| | | | |
|---|---|---|---|
| 9,498,366 B2* | 11/2016 | Burnett | ............ A61B 17/12099 |
| 2005/0273060 A1* | 12/2005 | Levy | ..................... A61F 5/0083 |
| | | | 623/23.67 |
| 2011/0004320 A1 | 1/2011 | Priplata et al. | |
| 2011/0082535 A1 | 4/2011 | Shin et al. | |

FOREIGN PATENT DOCUMENTS

| | | |
|---|---|---|
| WO | WO 2013/129088 | 9/2013 |
| WO | WO 2014/089129 | 6/2014 |

\* cited by examiner

APPLICATOR AND A METHOD FOR THE TRANSPYLORIC PLACEMENT OR REMOVAL OF A TRANSPYLORIC AND/OR A TRANSDUODENAL BYPASS DEVICE IN/FROM THE REGION OF THE PYLORUS OF A PATIENT

REFERENCE TO PENDING PRIOR PATENT APPLICATIONS

This patent application is a continuation-in-part of pending prior U.S. patent application Ser. No. 15/522,649, filed 27 Apr. 2017 by Trans-Duodenal Concepts GmbH for BYPASS DEVICE FOR THE TRANSPYLORIC CONDUCTING OF GASTRIC CONTENT INTO OR THROUGH THE DUODENUM, AND APPLICATOR FOR PUTTING SAME IN PLACE, which claims benefit of International (PCT) Patent Application No. PCT/IB2015/002005, filed 29 Oct. 2015 by Trans-Duodenal Concepts UG for BYPASS DEVICE FOR THE TRANSPYLORIC CONDUCTING OF GASTRIC CONTENT INTO OR THROUGH THE DUODENUM, AND APPLICATOR FOR PUTTING SAME IN PLACE, which claims benefit of German Patent Application No. DE 10 2014 015 919.1, filed 29 Oct. 2014, which patent applications are hereby incorporated herein by reference.

FIELD OF THE INVENTION

The invention is directed to an applicator and a method for the transpyloric placement or removal of a transduodenal bypass device for accepting chyme from the stomach and for bypass-type conducting of the chyme through the pylorus in or through the duodenum of a patient in the region of the pylorus of a patient. Preferably, the bypass device comprises a tubular, preferably radially collapsible and self-erecting transpyloric conducting element, which penetrates the pylorus, having a central conducting lumen for the chyme, and fixing elements for anchoring the transpyloric conducting element on the pylorus, consisting of an annular gastric anchor element, which is arranged on the gastric side or proximally to the pylorus, for anchoring the transpyloric conducting element proximally to the pylorus, having a gastric balloon segment, which regionally encloses a cavity of annular structure fillable with a medium, and an annular duodenal anchor element, which is located on the intestine side or distally to the pylorus in the duodenum, for anchoring the transpyloric conducting element distally to the pylorus, having a duodenal balloon segment, which regionally encloses a cavity of annular structure fillable with a medium; and an applicator for placing such a bypass device in a patient. An applicator element has the form of an endoscope or catheter with an elongated shaft, on the external surface of which the bypass device can be placed and/or plugged such that the applicator shaft entirely or partially penetrates the central conducting lumen of the bypass device.

BACKGROUND OF THE INVENTION

In Germany, approximately 90% of all diabetics, therefore 4.5 million people, are affected by type 2 diabetes, which is usually caused or accompanied by obesity (adiposity). This restricts the quality of life of the affected persons and induces numerous related illnesses. Industrial, emerging, and developing countries are affected in this case in a similar manner. Accordingly, a significant increase of nutrition-related diabetes illnesses is expected worldwide in the coming years. In parallel, the number of patients with Non-alcoholic Steato-Hepatitis (NASH) as another modality of the underlying metabolic syndrome increases especially in industrial countries.

Present therapies are predominantly directed to a medicinal regulation of the metabolism, there is no causal therapy in the strict sense. In addition to the medicinal metabolic regulation, in adipose patients suffering from diabetes, various methods for bariatric surgery have been established. In these methods, a differentiation is fundamentally made between restrictive (gastric band, gastric reduction, gastric balloon) and malabsorptive methods (bypass, duodenal switch, biliopancreatic diversion), wherein the greatest and most long-lasting successes are achieved by a combination of both method principles.

More recent experiences in bariatric surgery have shown that in particular operation methods which produce a bypass to the duodenum, in addition to the weight reduction, have a direct and immediate effect on the diabetic metabolic state, so that these methods are applied with increasing relevance in the treatment of diabetic patients.

However, the following facts argue against a large-scale application of operative bypasses of the duodenum:
- the severe and irreversible changes of the gastrointestinal tract, which are created by this operation;
- the fact that the long-term effects on the metabolism, bone stability, and tumor development are inadequately researched;
- that rare, but very severe and sometimes fatal complications can occur due to the interventions;
- that the patients require aftercare which is very costly in the long term, with monitoring of metabolic parameters; and
- that substantial treatment costs arise.

Because of the complications and costs linked to operative methods, endoscopy has set the goal of developing an implant for the treatment of diabetes and obesity, which, on the basis of duodenal bypass surgery, is based on conducting chyme through the duodenum by means of a tubular prosthesis placed in the duodenum.

The secretions from the pancreas and the gallbladder, which are required for the digestion of food, normally flow to the chyme in the region of the middle duodenum. Clinical studies have been able to show that bypassing the chyme through the duodenum (the first part of the small bowel) and prevention of a direct contact of food molecules to the mucosa by way of an artificially applied transduodenal bypass prosthesis leads to a suppression of the insulin secretion. This has a strong and immediate effect on the diabetic metabolism. Furthermore the delayed mixing of the chyme with the digestion-active secretions of the duodenum, leads on a direct path into the beginning of the jejunum, the digestion and therefore the resorption of the food components can be reduced, which, in addition to a resulting reduction of the body weight, has direct influence on the blood sugar level and therefore the insulin excretion. The precise mechanism of this phenomenon has not yet been researched, but its effectiveness has been proven.

The constructive design of such bypass tubular prostheses generally provides a mechanism which anchors the device in the region of the gastric outlet or sphincter (pylorus), and which takes up the food as completely as possible in the stomach or immediately adjoining the stomach. Additionally, the ring-like anchoring balloon is able to slow down the gastric emptying to the duodenum due to a disturbance of the peristalsis of the antrum muscle. This causes a delayed gastric emptying and a prolonged saturation feeling. This anchoring part is adjoined by a continuing tubular part, which conducts the chyme derived from the gastric side through the duodenum the into the beginning jejunum. The chyme is advanced in this case by the propulsive movements (peristalsis) of the duodenum in the tube, largely analogous to the natural transportation.

A bypass technology applicable by flexible-endoscopic implantation would be distinguished by the following advantages:
minimal invasiveness;
convenient reversibility, because it can also be removed again in an endoscopic manner; and
cost-effective applicability.

Various endoscopically placeable duodenal bypass devices with the goal of enteral resorption reduction are presently in testing. The systems are, depending on the structural design, either anchored in a position in the upper duodenum (duodenal bulb) directly adjoining the pylorus distally or they are positioned within the sphincter or extending beyond the pylorus into the stomach.

Regardless of the respective structural type, the anchoring mechanisms have to ensure, on the one hand, that a substantially liquid-tight terminus of the anchoring head unit of the device toward the duodenal wall or the pylorus is achieved, to prevent, as efficiently as possible, food components from passing the duodenum outside the tubular prosthesis and thus restricting its effectiveness. On the other hand, the forces which act by way of the anchoring mechanism on the respective applied organ walls have to be reduced enough that degenerative changes which could result in the course of time in bleeding or perforation, can be precluded. The balance between efficient anchoring and sealing and also organ-compatible placement is not least a challenge because of the special motility of the anatomical structures in the region of the transition from the stomach to the duodenum. The anchoring and sealing component of the bypass has to follow the contractile dynamics in the most compatible possible manner.

For approximately two years, an endoscopically placed, transduodenal tubular prosthesis of approximately 60 cm length, which is anchored using a stent-like metal basket in the upper duodenum within the so-called duodenal bulb, has been the focal point of antidiabetic treatment. This anchoring of the basket is performed by spiked extensions, which dig into the mucosa of the bulb and can be the cause of severe intermittent pain in the patient. The technique requires a permanent intake of stomach-acid-inhibiting medications (proton pump inhibitors=PPI) and can cause complications such as bleeding and perforation of the duodenal wall and liver abscesses. In particular, the removal of the implant can be risky because of the laterally protruding metal spikes.

In addition to such stent-based techniques for anchoring the bypass devices which take up the chyme, inter alia, balloon-based and ring-based, transpylorically placed anchor systems are being tested. With these, the pylorus, which marks the anatomical transition from the stomach into the duodenum, is taken between two balloon-like or annular structures in a type of clamping seal. A corresponding transpyloric anchoring by elastically self-erecting, O-ring type elements, which press against the pylorus on the stomach and duodenal sides, is described in U.S. Pat. No. 5,820,584. The two ring elements are integrated into the conducting element and each erect themselves proximally and distally to the sphincter due to the elastic intrinsic tension thereof. The channel-type passage opening of the pylorus is lined by an annular closed membrane unfolded between the rings. A tubular formation for conducting the stomach contents through the duodenum adjoins the ring placed on the duodenal side toward the small intestine. The elastic restoring force of the self-erecting ring components, which is required for the dislocation-secure, transpyloric positioning, and which exerts a permanent small-area force effect on the tissue on both sides of the sphincter, is problematic in the case of such techniques for anchoring. This sustained force action can also result in pressure-related damage or necrosis due to the required long-term application time periods of the transduodenal bypass. In addition, the endoscopic placement of such ring elements is relatively difficult.

US 2011/0004320 A1 describes by way of example a duodenal bypass device based on two tire-like, transpylorically placed fastening elements, which are connected to one another by stranded holding lines. The ring elements each have a rim-like inner tire, on which an elastically expandable balloon tubular element is seated, which expands primarily radially upon filling and thus acts as an anchoring abutment on the gastric and duodenal sides. In this case, upon filling, the balloon-like preformed abutment elements, which press against the pylorus on both sides, enter the state of a toroidal, elastic expansion, having an approximately circular cross section, wherein the pylorus itself remains substantially unloaded, because the completely unfolded buttress elements guide the forces thereof primarily onto the portions of the stomach or the duodenum adjoining the pylorus. The resulting load of these structures can lead to corresponding degenerative damage, as with the above-described, elastically self-erecting ring elements.

To achieve optimum tissue-compatible and organ-compatible, permanent placement of a transpylorically-positioned bypass device, an applicator and a method for a placement of such a bypass device would be desirable which reduces the stress or radial forces on the structures adjacent to the pylorus as well as on the pylorus itself. Especially, an applicator and a method for a minimal invasive placement of such a bypass device would be desirable.

Furthermore, the transpyloric anchoring should be capable of independently adapting itself as much as possible to functional changes of the sphincter. In the ideal case, the motility of the pylorus should remain unimpaired and/or the pyloric closure and a corresponding deformation of the transpyloric components of the device can take place with the least possible contraction force.

Furthermore, it should be possible in bypasses of the transpyloric type to make the force which loads the pyloric structures and the structures adjoining the pylorus adjustable from outside the body and/or to adapt it to the individual in the course of time.

For an advantageously efficient weight-reducing effect of the device, bypass devices which link the (malresorptive) bypass function with other action principles, for example, a (restrictive) reduction in size of the stomach volume, would also be significant.

Besides of a primarily transduodenal bypass function of the device, the transpyloric head unit of the device can also perform as a primarily transpyloric bypass. In this case, the transduodenal conducting tube would not be part of the design, the transpyloric bypass would consist only of a transpyloric unit. The transpyloric bypass can have a beneficial effect for treatment of a delayed emptying of the stomach, as it can be observed e.g. in cases of oesopgaheal resection of a tumor, whereby upper portion of the stomach is pulled upwards into the chest cavity of the patient, connecting there to the resected end of the esophagus. The central, chyme-conducting shaft component of such a transpyloric bypass is preferably made of elastic material, having stronger performing self-erection properties, keeping the transpyloric segment of the bypass tendentially open, instead of allowing for a radial collapse of the segment under normally acting sphincter tone. Despite of the deployment of the transduodenally conduction hose tube from the transpylorically positioned head unit, the applied technology and method of placement in and removal from the patient's body are identical with the herein described device for transduodenal bypass.

SUMMARY OF THE INVENTION

The stated problem is solved by an applicator for a releasable coupling of a transpyloric and, if applicable, transduodenal bypass device comprising a tubular, preferably radially collapsible and self-erecting transpyloric conducting element, which is or has to be placed in a patient in such a way that it penetrates the pylorus of the patient and is provided with a central conducting lumen comprising an upstream mouth to be placed antegrade of the pylorus and a downstream mouth to be placed retrograde of the pylorus, for (i) accepting the chyme from the stomach, for (ii) bypass-type conducting of the chyme through the pylorus and, if applicable, through the duodenum or a part of the duodenum, and for (iii) releasing the chyme in or beyond the duodenum of the patient, to an endoscope or a catheter having an elongated shaft, on the external surface of which the bypass device can be placed and/or plugged in order to insert the bypass device under direct guidance of the endoscope or catheter from the outside of the patient's body in an antegrade way through the upper digestive tract into the stomach, or to remove it in a retrograde way through the upper digestive tract, wherein the applicator comprises a tubular coupling element, which is or can be slid onto the external surface of the shaft surrounding it, and which entirely or partially penetrates the central conducting lumen of the bypass device, thereby bridging a gap between the external surface of the shaft and an internal surface of the central conducting lumen of the bypass device.

The bypass device can be fixed on the shaft or released therefrom by the user by way of a preferably separate carrier and coupling mechanism in the form of an applicator, which is or can be attached to the endoscope or applicator shaft.

Preferably, the tubular coupling element of the applicator is in the form of a cuff, sleeve or manchette. Especially in such embodiment, the bypass device is held on the shaft of the endoscope or catheter by a clamping action of the applicator, wherein an annular, extracorporeally fillable, gap-bridging balloon of the applicator is provided for the clamping fixation of the bypass device on the outer side of the shaft of the endoscope or catheter, which, when the bypass device is placed or plugged on, is located in the annular gap between the applicator shaft, on the one hand, and the transpyloric conducting element, on the other hand, in particular, radially inside the fixing unit and/or radially inside the front end of the transduodenal conducting tube.

The inner surface of the tubular coupling element of the applicator can be in the shape of a hollow cylinder.

On the other hand, the outer surface of the tubular coupling element of the applicator may comprise a cylindrical section.

Furthermore, the outer surface of the tubular coupling element of the applicator may comprise at least one local radial enlargement, especially at the proximal end of the tubular coupling element.

Such local radial enlargement can be designed in the shape of a toroidal bulge.

The invention recommends that the bypass device be held reversibly, i.e., detachably, by the applicator on the shaft of the endoscope or catheter.

Besides other embodiments, the tubular coupling element of the applicator may comprise a releasable fixing mechanism for the bypass device which is connected to an extracorporeal control device, i.e. via a steering wire or a bowden control cable. Other release mechanisms can be used, e.g. driven by lock and release functions, operated from the outside of the body.

Furthermore, a coupling between a bypass device and the shaft of an endoscope or catheter can be implemented, for example, by a tubular coupling element of the applicator which is formed of at least one balloon, especially as an externally fillable, hollow-cylindrical balloon, which acts between the endoscope shaft and the bypass device and is drawn onto the shaft of the endoscope. Pressure is applied thereto for the duration of the insertion and application of the bypass and it thus holds the bypass device securely in position. The coupling unit is mechanically secured onto the shaft outside of the applicating endoscope or catheter, either by an elastic retraction of a tubular elastic layer inside the central lumen of the coupling unit, effecting a sufficiently strong fixation on the applicating unit, or the coupling unit is performed by a second hollow-cylindrical balloon, keeping the deployment unit secured in position on the outside surface of the applicator, whereby the inner fixation balloon is independently inflated from the outer coupling balloon.

In one embodiment of the invention, one or several balloons each only partially surround the shaft of the endoscope or catheter, it/they can be brought into contact with the inner side of the transpyloric conducting element of the bypass device, when the bypass device is placed or plugged on the shaft of the endoscope or catheter.

In another embodiment of the invention, at least one annular balloon entirely surrounds the shaft of the endoscope or catheter and is brought in contact with the inner side of the transpyloric conducting element of the bypass device, when the bypass device is placed or plugged on the shaft of the endoscope or catheter.

The invention further recommends that a cross section through the at least one annular balloon of the tubular coupling element of the applicator in a longitudinal direction of the tubular coupling element is in the shape of an L.

In more detail, the longer leg of such L-shaped cross section through the at least one balloon of the tubular coupling element of the applicator may belong to the cylindrical section of the tubular coupling element, whereas the shorter leg of the L-shaped cross section through the at least one balloon of the tubular coupling element of the applicator may belong to the radial enlargement or toroidal bulge of the tubular coupling element.

All coupling and fixing components described in the context of the present invention are not only limited to cylindrical, hollow structures, but can also be designed as one or more segments within the circumference of a contact surface, especially wherein each segment extends only along a partial circumference of the contact surface.

At least one balloon may be connected to a supply line extending parallel to the endoscope or catheter, in order to enable an inflation or deflation of the balloon.

A valve arranged in the supply line for the at least one balloon, preferably a check valve to be opened manually, enables the aeration and deaeration of the balloon, which clamps the bypass device on the shaft of the endoscope or catheter.

If the at least one balloon is inflated, the bypass device is fixed onto the shaft of the endoscope or catheter, whereas the bypass device is released from the shaft of the endoscope or catheter, if the at least one balloon is deflated.

According to the invention, the bypass device is held by clamping on the applicator by the at least one gap-bridging balloon which is located in the annular gap between the shaft of the endoscope or catheter on the one hand, and the transpyloric conducting element of the bypass device on the other hand, when the bypass device is placed or plugged on the shaft of the endoscope or catheter.

The tubular coupling element of the applicator should be fixed or fixable to the shaft of the endoscope or catheter, in order to avoid undesired displacements between the applicator and the shaft of the endoscope or catheter.

Preferably, the tubular coupling element of the applicator may be held reversible or detachably on the shaft of the endoscope or catheter. Such embodiment enables a separation of the applicator from the endoscope or catheter if the latter shall be used otherwise.

The invention further provides that the tubular coupling element of the applicator is or can be fixed or detachably fixed on the shaft of the endoscope or catheter by a fixing mechanism for the shaft.

In a first embodiment, such fixing mechanism for arresting the tubular coupling element of the applicator on the shaft of the endoscope or catheter may comprise a sleeve, cuff or manchette made of an elastic material which contracts the sleeve, cuff or manchette around the shaft in order to achieve a frictional engagement with the shaft. Preferably, the initial length of the inner perimeter of an annular sleeve, cuff or manchette should be less than the length of the outer perimeter of the shaft of the endoscope or catheter.

On the other hand, to avoid a disengagement of such sleeve, cuff or manchette from the inner side of the tubular coupling element of the applicator, it is preferred that the sleeve, cuff or manchette is fixedly connected to the inner side of the tubular coupling element of the applicator.

In another embodiment, the fixing mechanism for arresting the tubular coupling element of the applicator on the shaft of the endoscope or catheter may comprise one or several balloons which are arranged on the inner side of the tubular coupling element of the applicator.

Such at least one balloon which is arranged on the inner side of the tubular coupling element of the applicator should be connected to a supply line extending parallel to the endoscope or catheter, to enable an inflation or deflation of the one or several balloons, in order to arrest or release the tubular coupling element of the applicator on/from the shaft of the endoscope or catheter.

A valve, preferably a check valve to be opened manually, enables the aeration and deaeration of the at least one balloon, which clamps the bypass device on the applicator shaft.

An applicator is furthermore preferably characterized by flushing openings, preferably distal to the gap-bridging balloon, through which liquid can be flushed extracorporeally into the duodenum via a flushing line extending along the applicator, to unfold the distal section of the conducting element.

If an applicator according to the invention comprises an x-ray-opaque marking in the region of the distal end, the location thereof can be checked as the applicator is advanced by the shaft of the endoscope or catheter.

The applicator according to the invention is preferably adapted for the placement or removal of a transpyloric and, if applicable, transduodenal bypass device for accepting chyme from the stomach and for bypass-type conducting of the chyme through the pylorus in or through the duodenum of a patient, comprising a tubular, preferably radially collapsible and self-erecting transpyloric conducting element, which penetrates the pylorus, having a central conducting lumen for the chyme, wherein the bypass device comprises fixing elements for anchoring the transpyloric conducting element on the pylorus, comprising an annular gastric anchor element, which is arranged on the gastric side or proximal to the pylorus, for anchoring the transpyloric conducting element proximally to the pylorus, having a gastric balloon segment, which regionally delimits a cavity of annular structure fillable with a medium, and also comprising an annular duodenal anchor element, which is located on the intestine side or distally to the pylorus in the duodenum, for anchoring the transpyloric conducting element distally to the pylorus, having a duodenal balloon segment, which regionally delimits a cavity of annular structure fillable with a medium.

Such a bypass device may be placed at or in the pylorus of a patient by use of an applicator according to a method which comprises the following steps:
  a) sliding or plugging the applicator onto the shaft of the endoscope or catheter;
  b) placing or plugging the bypass device on the applicator, so that it penetrates the central conducting lumen of the transpyloric conducting element of the bypass device;
  c) fixing the bypass device by activating a fixation mechanism, especially by filling a gap-bridging balloon between the applicator and the inner side of the conducting lumen of the transpyloric conducting element of the bypass device;
  d) inserting the bypass device by means of the endoscope or catheter into the stomach of a patient in an antegrade way through the upper digestive tract;
  e) partially or completely filling the gastric balloon segment of the gastric anchor element;
  f) inserting the distal section of the conducting element through the pylorus, until the entirely or partially filled gastric balloon segment rests proximal to the pylorus and noticeably resists a further advance of the bypass device;
  g) filling the duodenal balloon segment to anchor the duodenal anchor element distal to the pylorus;
  h) releasing the distal section of the conducting element; and
  i) detaching the bypass device by deactivating the fixation mechanism, especially by deaerating the gap-bridging balloon between applicator shaft and inner side of the conducting lumen.

In the process, liquid can be flushed extracorporeally into the duodenum between steps h) and i) via flushing openings arranged on the applicator shaft distal to the gap-bridging balloon, to unfold the distal section of the conducting element. In order to prevent an undesired reflux of flushed fluid into the stomach, the gap-bridging balloon can be inflated inside the open lumen of the trans-pyloric head-unit, performing a sealing occlusion.

Furthermore, after step i), the supply lines to the balloon segments can be dropped into the stomach and remain therein until the bypass device is removed. Alternatively, the supply lines can be mechanically decoupled from valve-like, self-closing components, which are integrated into the gastric portion of the bypass device, or can trimmed close to the gastric device portion by endoscopically guided scissors, after the lumina of the supply lines have been closed by welding or by filling the lumina up with a gap-filling, spontaneously curing glue.

Furthermore, a bypass device may be removed from the pylorus of a patient by use of an applicator according to a method which comprises the following steps:
  a) sliding or plugging the applicator onto the shaft of the endoscope or catheter;
  b) inserting the endoscope or catheter into the stomach of a patient;
  c) placing or plugging the bypass device on the applicator, so that it penetrates the central conducting lumen of the transpyloric conducting element of the bypass device;
  d) fixing the bypass device by activating a fixation mechanism, especially by filling a gap-bridging balloon between the applicator and the inner side of the conducting lumen of the transpyloric conducting element of the bypass device;
  e) deflating the duodenal balloon segment to release the duodenal anchor element from the pylorus;
  f) retracting the distal section of the conducting element through the pylorus;
  g) deflating the gastric balloon segment of the gastric anchor element; and
  h) removing the bypass device by means of the endoscope or catheter from the stomach of the patient in a retrograde way through the upper digestive tract.

This applicator is especially adapted for a transpyloric placement and/or removal of a bypass device wherein the gastric balloon segment and/or the duodenal balloon segment encloses (enclose) the transpyloric conducting element radially on the outside, is (are) not closed along a circumferential line in the toroidal direction, i.e., has (have) only twofold connectivity, and is (are) connected to the conducting element so that the latter forms a part of the enclosure of the relevant, toroidal cavity, wherein the conducting element is formed or reinforced at least in its region enclosing the gastric and/or duodenal cavity such that it has there a structural stability or self-erecting capability which is at least equal to or greater than that of the relevant balloon segment in the immediate surroundings of the conducting element.

The present invention therefore describes an endoscopically placeable, transpylorically-positioned bypass device for conducting chyme from the stomach through the duodenum, which is preferably based on very thin-walled, but dimensionally-stable, complexly formed balloon films. The embodiments of the invention described hereafter enable the radial expansion of the transpylorically-anchored balloon segments upon application of filling pressure to be adjusted with good reproducibility to a target amount which is not to be exceeded. Due to the construction-related generation of a rolling movement of the balloon segments, which is oriented in the axial action direction onto the shoulder surfaces of the pyloric sphincter, a particularly advantageous combined radially and axially acting anchoring and sealing action can be achieved.

Due to the completely or nearly completely embodied preforming of all segments of the balloon sleeves to the dimensions required for the function thereof in situ and also due to the use of less volume-expandable film materials, which are substantially dimensionally-stable upon application of filling pressure, the functionally required geometry and mechanical characteristic of the balloon components integrated in the anchoring device already develop when the internal pressure prevailing in the transition region of stomach and duodenum is slightly exceeded. The balloon bodies formed according to the invention thus do not require a force-intensive elastic expansion of the balloon wall to unfold the function thereof and can thus be placed in a substantially pressure-neutral and therefore gentle manner.

Upon increase of the filling pressure, due to the particular hardness of the film material used and/or the lesser volume expandability thereof (compliance), the radial expansion of the balloon film remains limited, while the applied force preferably passes transitions into an axially-oriented pressing action of the balloon or buttress segments, which roll against one another axially. Depending on the respective filling pressure, the axial force effect acting on the pylorus can thus be adapted by the user over an optimum broad range.

The invention furthermore describes particular embodiments of the transpyloric segment of the device, which is placed inside the pylorus channel and connects the gastric and duodenal buttress elements. In this case, maintaining the closing capability of the pylorus as much as possible and at the same time precluding axial twists of the conducting element is paramount. This is enabled in a preferred embodiment of the bypass device by a coaxial double-layered tube film arrangement, which, by way of specifically attached, punctiform or linear connections of the two concentric film layers, driven by the force currently acting on the balloon elements, causes both lumen erection of the conducting pyloric segment and also the axial untwisting thereof.

To improve the weight-normalizing effect, beyond the duodenal bypass action, the device according to the invention can optionally be equipped in its embodiment such that the balloon segment, which is placed in the stomach and primarily acts as a buttress therein, is formed in a diameter or volume amount which has a space-occupying effect in the pylorus-proximal antrum of the stomach and triggers a feeling of fullness via a moderate, but permanently acting stretching of the wall of the antrum and/or shifts the time of a feeling of fullness forward upon food intake. This restrictive effect can alternatively also be reinforced by an additional, separately fillable, for example, toroidally-formed balloon element, which adjoins the described transpyloric anchor device on the stomach side and is accordingly space-occupying.

To achieve an advantageously prompt, elastically-acting lumen erection of transpyloric conducting segments, polyurethane (PUR) is preferably used as the base material for producing the corresponding components. The shaft element extending through the pylorus, which in a preferred construction carries a balloon component on the gastric and duodenal sides, can be formed, for example, from a tubular body or also injection molded. Preferably polyurethanes of the degree of hardness range Shore 70 A to 90 A are used for the balloon-carrying shaft element. The elastic deformation and erection properties of the shaft element can be modified by additional sleeve-type or tubular elements made of, for example, foam, fiber, net, or gel. Such modifications can be required above all in the region of the terminal components of the conducting shaft element, which carry an annular or cylindrical balloon. The modifying structures are either inserted into the lumen of the conducting element or alternatively installed on the outer circumference thereof. The conceptually desired radial folding capability of the part of the conducting element which is placed directly at the pylorus is to be maintained as much as possible in the case of corresponding modifications.

The wall of the balloon elements integrated in the transpyloric anchoring and sealing head unit of the device also preferably consists of polyurethane. The preferred durometers range from Shore 80 A to 95 A, on the one hand, and Shore 55 D to 70 D, on the other hand. Above all, polyurethanes of the hardness Shore 95 A and 55 D to 65 D ensure the stability required for the reliable function, even with ultrathin-walled design in the low micrometer range, even at higher filling pressures. For the permanent placement in the acid milieu of the stomach, higher durometers of aromatic TUR types are preferred. To further improve the acid resistance, the TUR-based balloon sleeves can optionally be provided with an additional outer layer made of PEBAX or Polyamide (PA). The combination of the two materials can be ensured, for example, by a corresponding coextrusion of the raw tube material, which is formed by blow-molding to form the balloon.

A further advantage of the extremely thin-walled embodiment according to the invention of the anchoring and sealing balloon elements is the low overall size enabled thereby. In spite of the relatively complex structure of the device, the described film-based bypasses can be conveniently applied endoscopically. The device, which is applied to the outer surface of the endoscope shaft and is thus transported through the throat and the esophagus into the stomach of the patient, is carried on the endoscope back in the evacuated state in an optimally slim manner, which does not obstruct the passage.

The parapyloric portions of the device are preferably provided with x-ray-opaque structures, which enable the confirmation of the transpyloric location in the image converter if needed.

The fillable elements of the device are filled extracorporeally in the preferred construction via sufficiently long-dimensioned tubular supply lines.

The transpyloric head unit adjoins the transduodenal conducting tube unit, which represents the actual bypass, toward the duodenum. The duodenal conducting tube unit is attached in a space-saving manner, preferably gathered like folded bellows, on the duodenal end of the transpyloric unit and/or directly adjoins the duodenal balloon or buttress segment, correspondingly arranged in a space-saving manner.

The optional construction according to the invention of the transpyloric head unit from preferably continuously formed balloon sleeves, which in the ideal case comprise both portions of the gastric, the duodenal, and also the central pyloric segment of the head unit, is furthermore advantageous because potentially critical joints can be reduced. The invention describes corresponding embodiments, which consist nearly completely of a single balloon sleeve and which reduce the number of the joints required for providing the various compartments within the head unit to a minimum by corresponding eversion or back-eversion of the balloon ends.

To generate the optionally described, axially-oriented counter-rolling movement according to the invention of the balloon or buttress components acting on the gastric and duodenal sides, a preferably cylindrically formed balloon element is applied during the mounting to a shaft element which carries the balloon, such that the shaft ends of the balloon are offset on the shaft by a certain amount, for example, 30-60% of the freely unfolded cylindrical length of the balloon, oriented toward one another. The balloon thus fixed on the shaft then rolls into a low-tension middle position upon filling via the two balloon ends, which are offset toward one another or approach one another. The balloon body can be axially deflected from this rest position, wherein an axial force acting opposite to the deflection direction has to be overcome. If the fixing points of a balloon body applied in this manner are positioned close enough to an opening to be closed, the shoulder of the balloon oriented toward the body cavity or opening detaches toward it in the manner of an axially acting rolling movement and holds the corresponding buttress element on the other side of this body cavity or opening under a corresponding tension, which is axially oriented toward the body cavity or opening to be sealed. This effect exists with balloon elements which are counter-rolling, structurally separate from one another and are both attached on one side adjacent to a body cavity or opening and also on both sides of a body cavity or opening, and are optionally fillable in a separate or communicating manner.

Furthermore, there is a waisted embodiment of a formed balloon body, which has a central, tapered section between two terminal balloon segments having a sealing action, which is not connected to the balloon-carrying shaft and is placed within the sphincter opening, wherein the terminal balloon segments, in the event of corresponding offset of the balloon ends oriented toward one another on the shaft, are also distinguished by a rolling movement, which is oriented from the lateral toward the central waist and has a clamping and sealing action.

The present invention furthermore describes a self-erecting mechanism of coaxially applied tube film layers connected to one another by punctiform connections. In this case, a part of the filling medium can be displaced into the free space between the concentric film layers. This section then erects itself in the manner of a self-erecting, air-stabilized tubular body, which is quilted like a mattress. Upon decreasing filling pressure, this part of the device relaxes, and the conducting lumen can contract under the loading force of the closing pylorus to form a minimally space-occupying, non-dilating structure.

In one particular embodiment, the present invention combines the principle of the axially-oriented counter-rolling movement with the mode of action of the concentric film arrangement, which is self-erecting upon application of pressure.

Preferably, both the gastric and also the duodenal buttress element comprise such a fillable balloon segment. The central, transpyloric segment can have the described, concentrically arranged film construction and is preferably connected in a freely communicating manner to both buttress balloon segments, or—less preferably—only to the gastric balloon compartment.

In one particularly advantageous embodiment, all three segments are formed from a single molded blank and subsequently closed by partial or also complete back-eversion and/or inversion of the balloon ends to form a single, communicating space or also, in conjunction with stabilizing tube or ring components, compartmented to form multiple communicating partial spaces. By way of a punctiform or linear or web-like connection of the concentric film layers in the transpyloric segment exposed in the sphincter, this segment achieves its lumen-erecting and/or lumen-untwisting action.

In addition to the preferred embodiment of the transpyloric segment of the device as a self-erecting, concentric film arrangement, the transpyloric component can also be formed, for example, as a continuous tubular element, which has an elastic effect such that under contraction of the pylorus, it collapses to form a structure of smaller diameter and spontaneously erects into the opening pylorus upon decreasing tonus. The elastic self-erection of the tubular element has to withstand the pressure which acts in the balloon on the tubular element in this case and preclude a constriction of the drainage lumen. To optimize the self-erecting properties, the tube cross section can be provided with a stabilizing annular or coiled corrugation, which, with equal elastic restoring force, enables a reduction of the wall thickness of the element which is advantageous for the placement. In addition to the described corrugation of the tubular element, the tube can also consist, as a combined structure, of a continuous tube shaft, having a material layer, for example, of a netlike, fibrous, or foamed composition, which stabilizes, jackets, or also lines the shaft. The modification of the elastic active components of the individual material layers which is thus possible ensures an ideal adjustability of the closing and opening force, with which the transpyloric tubular body closes upon a contraction of the sphincter or which develops therein in the case of an opening sphincter, respectively.

At least one balloon segment should not form a completely closed torus, but rather should have at least one free edge extending circumferentially, which is closed in a ring shape and presses against the transpyloric conducting element. By means of this free edge, the relevant balloon segment can be positioned precisely on the conducting lumen and, in interaction with its preforming, its behavior during filling can be precisely influenced.

The at least one free edge of the balloon segment, which extends circumferentially and is closed in a ring shape, may be connected, in particular glued or welded, to the transpyloric conducting segment to form a seal.

At least one balloon segment can be everted (multiple times) in the region of at least one free edge which is connected to the transpyloric conducting segment to form a seal, such that it presses flatly with its inner side facing toward the relevant cavity against the transpyloric conducting element.

At least one balloon segment can be everted inwardly into the relevant balloon segment in the region of each of its two free end edges.

Preferably, a second, opposing eversion, i.e., in the direction out of the relevant balloon segment, is located between a free end edge and the eversion thereof into the relevant balloon segment.

Further advantages result in that a balloon segment is preformed such that it has different circumferential lengths in certain annular sections, in particular in that it has a smaller circumferential length in the region of each of its two free end edges than in a region of the balloon jacket located in between, which forms an outwardly everted section of the balloon segment. As a result, the shape of the unfolded balloon segment that is free of external influences may equally be determined and/or influenced as a result of a balloon segment being pre-formed, such that it has different thicknesses in certain annular sections, in particular, in that it has a greater thickness in each of its two free end edges than in a region of the balloon jacket located in between, which forms an outwardly everted section of the balloon segment.

Because a balloon segment is preformed such that, with the cavity expanded up to its preformed volume, the cross section through this cavity has a greater axial extension than in the radial direction, in relation to the longitudinal axis of the conducting element, a predominant extension of the unfolded balloon segment in the axial direction is predetermined. An optimum capability results therefrom of being able to roll back in the axial direction to provide space for the pylorus, on the one hand, but also to develop a pressing force oriented against this yielding movement, to thus anchor the conducting element. In this case, the sealing force acts in a focused manner on the shoulder surfaces of the pyloric sphincter ring, where a form fit can then be formed, which counteracts a slipping of the conducting element out of the region of the pylorus.

Accordingly, the force exposure on the structures of the stomach and the duodenum adjoining the pylorus, even at a higher filling pressure of the balloon segments, is reduced to a permanently organ-compatible amount, in particular to a pressure below the filling pressure of the balloon segments.

The fill level of the balloon segments and/or the filling level thereof, and therefore the axial sealing force acting on the pylorus should be able to be adjusted extracorporeally, optionally with the aid of a pump and/or a manometer.

As the filling pressure within one or both balloon segments, the invention provides values of 10 mbar to 100 mbar above the atmospheric pressure, in particular, values of 20 mbar to 80 mbar above the atmospheric pressure, in particular, values of 30 mbar to 60 mbar above the atmospheric pressure.

The invention may be refined in that, within at least one cavity which is regionally delimited by a balloon segment, an additional inner cushion or balloon element is arranged, which is filled or fillable using a different filling medium than that of the receiving cavity itself.

Such an inner cushion or balloon element should be peripherally fixed, in particular welded or glued, to form a seal on the transpyloric conducting element, so that it cannot slip.

At least one inner cushion or balloon element preferably encloses a smaller volume and/or is preformed having a smaller volume than the external balloon segment which supports the cavity receiving it, so that within the outer balloon segment, in addition to the inner cushion or balloon element, a (remaining) cavity also remains, which is preferably fillable with a compressible medium such as air or gas and can then cling in an optimum and preferably sealing manner to the inner side of the relevant organ.

It has proven to be effective for at least one inner balloon element to be fillable with a liquid medium. A maximum structural stability thus results—in conjunction with a comparatively hard balloon material, for example, polyurethane—whereby undesired detachment of such an anchoring part from the provided anchoring point is virtually precluded. The outer balloon should therefore be filled with air, i.e., a compressible medium, in order to be able to cling optimally to the inner side of the relevant organ and be able to seal it.

The conducting element experiences a reinforcement in the region of at least one inner balloon element by a sleeve or a preferably annular or spiral spring element. Such an element is capable, without constricting the conducting lumen, of also being able to support completely unfolded anchoring elements, without collapsing.

The invention recommends that at least one inner balloon element be toroidal-shaped, i.e., with threefold connectivity. Its structural stability is thus increased and an effect which constricts the conducting lumen upon filling the relevant, inner balloon element is minimized.

At least one inner balloon element, in the region of one or both of its annular circumferential end edges, should press flatly against the transpyloric conducting element and be fixed thereon, for example, glued, with its inner side, which faces toward its filling medium.

The invention may be refined in that the gastric balloon segment and the duodenal balloon segment are united to form a single balloon, which is preformed in a dumbbell shape, having an approximately central, circumferential extending constriction to accommodate the pylorus sphincter. Therefore, the shape of the pylorus can be optimally re-created in the manner of a negative mold.

The invention is furthermore distinguished by at least one supply line or a filling tube to at least one toroidal cavity, so that one or both balloon segments are fillable after the placement of the transpyloric bypass device, in particular, the transpyloric conducting element and/or the fixing unit. In order for the oral or proximal end of such a supply line or such a filling tube to be insertable into the stomach and/or droppable therein, at least one supply line to at least one toroidal cavity, in particular, a filling tube, should be provided with a check valve.

Because the transpyloric conducting element connects the gastric anchor element to the duodenal anchor element, the arrangement experiences an optimum structural stability in any case in the axial direction.

The wall thickness of the transpyloric conducting segment should be thicker in any case in its head region, which penetrates the pylorus, than the wall thickness of the gastric balloon segment on its periphery, which bulges radially outward and/or than the wall thickness of the duodenal balloon segment on its periphery, which bulges radially outward, for example, at least twice as thick, preferably at least 5 times as thick, in particular at least 10 times as thick. The mutual location of the two anchor elements is thus predetermined.

The transpyloric conducting element can be preformed in a tube shape, so that it does not collapse upon filling of one or both balloon segments under the filling pressure therein, but rather erects itself into an approximately cylindrical shape in a state free of external forces.

Because the transpyloric conducting element is wavy or corrugated, its self-erecting properties are improved, and in addition it can be collapsed or gathered like a folded bellows.

The transpyloric conducting element can be stiffened in the region of one or both balloon segments by a sleeve or an annular or spiral spring, so that it does not collapse under the filling pressure therein upon filling of one or both balloon segments.

Furthermore, the possibility exists that the transpyloric conducting element has a coaxial double-layered tube film arrangement, or that it consists of such a coaxial double-layered tube film arrangement.

The two tube film layers of such a transpyloric conducting element constructed as double-layered should be at least regionally connected to one another, preferably by punctiform, linear, or planar connections, in particular in the section which penetrates the pylorus. The outer layer is pressed outward by a (low) inner overpressure between these two tube layers and in the process carries along the inner tube layer as a result of the connections. The conducting lumen is therefore by its nature open, yet can be easily compressed if needed by the pylorus due to the low filling pressure.

Production-related advantages can result by forming the tube film layers of the transpyloric conducting elements together with one or more balloon segments from a common film tube.

At least one x-ray-opaque marking, which is placed on the transpyloric conducting element and/or in or on one or both fixing elements proximal and/or distal to the pylorus, is used to determine the correct transpyloric location of the transpyloric bypass device, in particular the transpyloric conducting element and/or the fixing element or elements.

BRIEF DESCRIPTION OF THE DRAWINGS

Further features, properties, advantages, and effects based on the invention result from the following description of preferred embodiments of the invention and on the basis of the drawing, wherein.

DETAILED DESCRIPTION OF THE PREFERRED EMBODIMENTS

Figure 1:
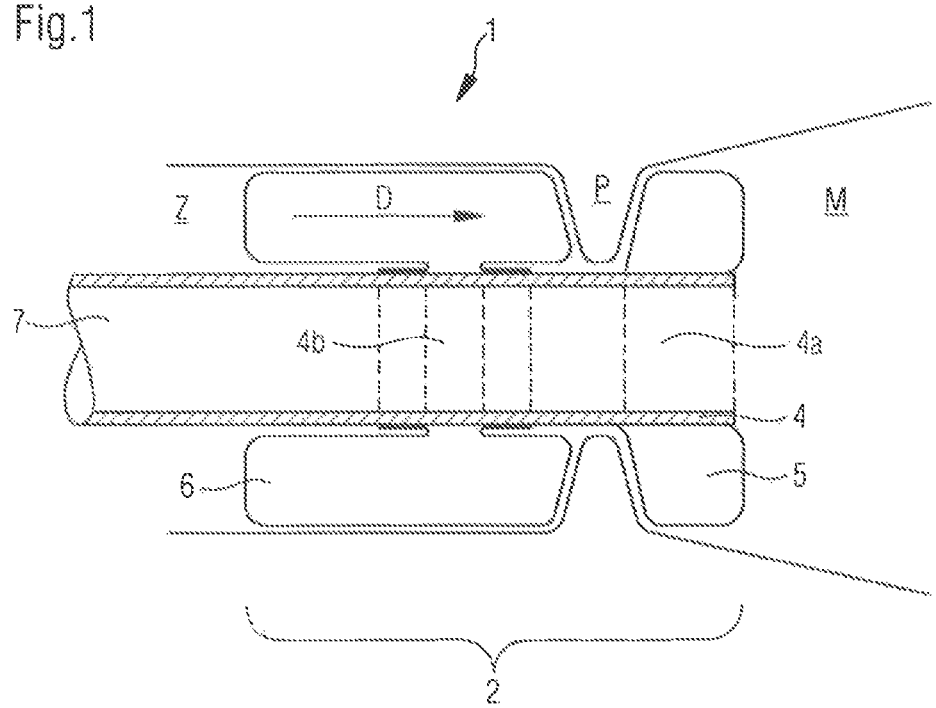
FIG. 1 shows an embodiment having a back-rolling balloon component attached on one side and opposing, non-back-rolling balloon element.

FIG. 1 schematically shows a bypass device 1 according to the invention and describes by way of example the required components and structural features for generating a rolling movement D, which is oriented toward the pylorus P, of a fillable balloon element.

The fixing unit 2 is shown, which is placed beyond the pylorus (transpylorically), of the bypass device, which receives the chyme from the stomach M and conducts it through the pylorus P into the duodenum Z. The unit which fixes the bypass in its transpyloric position has in the center a conducting element 4, which carries an anchoring buttress element 5 on its gastric end 4a and is equipped on its duodenal end 4b with a duodenal balloon element 6, which rolls toward the buttress element in the filled state, is formed in a specific manner, and is fixed on the conducting element. A tube element 7, which conducts the chyme through the duodenum, adjoins the duodenal end 4b of the conducting element.

Figure 1A:
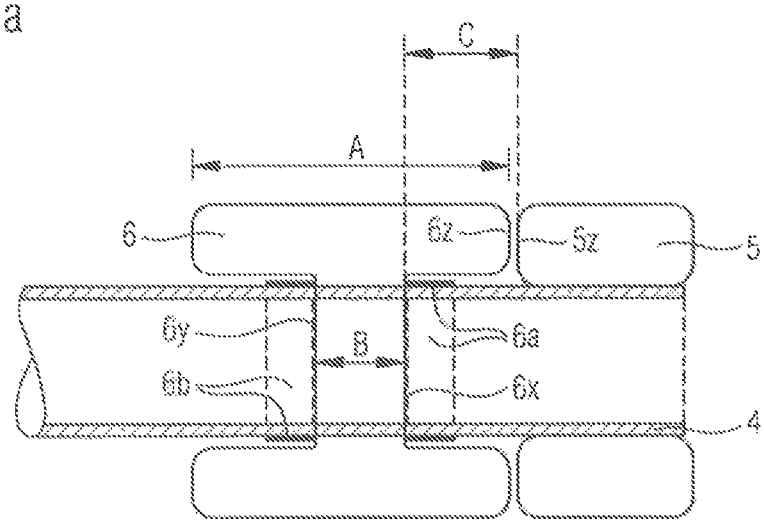
FIG. 1a shows the configuration of the back-rolling balloon element shown in FIG. 1 of the head unit which fixes the device, in the freely unfolded state outside the body.

FIG. 1a shows the transpyloric fixing unit 2 described in FIG. 1 in the filled state outside the body. The counter-rolling duodenal balloon element 6 is shown here in a preferably cylindrical shape, wherein the balloon material used has a composition such that upon filling in a pressure range from approximately 20 to approximately 100 mbar, from the preformed state, it passes through a radial expansion of the cylindrical diameter of not greater than 10%, and particularly preferably not greater than 5%. The formed cylindrical diameter of the duodenal balloon element 6 is preferably to be dimensioned so that it does not dilate the wall of the duodenum adjoining the pylorus, and/or only puts it under moderate expansion or tension, which is limited by the described expansion properties of the balloon. The filling pressure resulting in the case of an expansion of the duodenal wall in the balloon 6 should not exceed 50 mbar.

The length of the cylindrical contact surface A should preferably be approximately 1 to 4 cm and particularly preferably 2 to 3 cm. The distance B between the balloon ends 6a and 6b is preferably to be 20 to 60% and particularly preferably 20 to 40% of the length of the contact surface A. The terminal edges 6x and 6y of the balloon ends oriented toward the balloon interior are decisive for the resulting axial rolling travel of the balloon mounted on the conducting element 4. The distance B is accordingly defined as the distance between the terminal edges 6x and 6y.

The fixing of the balloon on the conducting element 4 is preferably to be performed such that the terminal edge 6x is spaced apart by the absolute value of the section C from the pyloric shoulder 5z of the gastric buttress element 5, wherein C is preferably not to be greater than the absolute value which results from A/2−B/2+5 mm. This absolute value represents a state of the filled balloon 6, in which the balloon is positioned in the central neutral state via the terminal edges 6x and 6y and the resulting gap between the pyloric shoulder 6z of the duodenal balloon element 6 and the gastric shoulder 5z of the gastric buttress element has a width of 5 mm, which approximately corresponds to the anatomical width of the pyloric sphincter. In a particularly preferred embodiment, the section C has an absolute value which is less than A/2−B/2+5 mm, can extend up to mm, or also has an absolute value which is less than A/2−B/2.

Figure 1B:
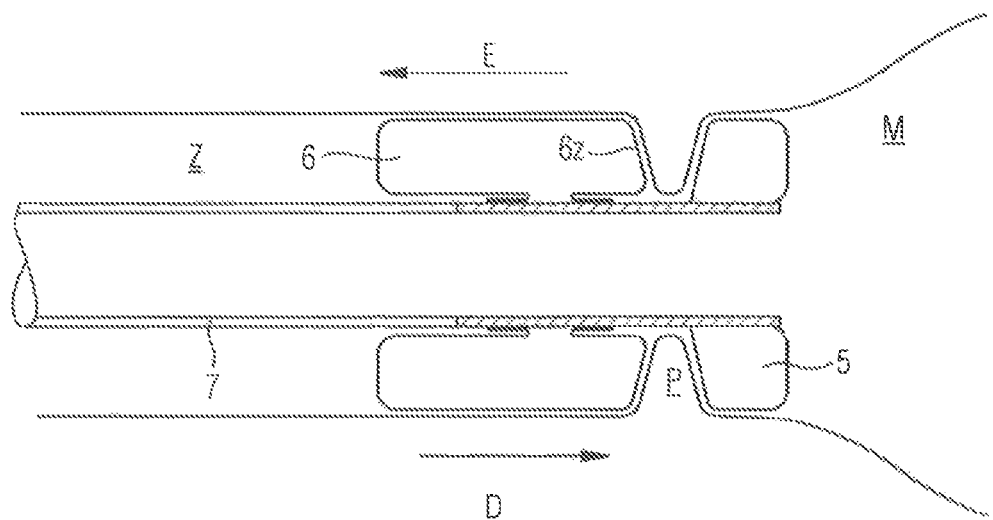
FIG. 1b shows the above-described head unit in situ and illustrates the axially-oriented back rolling or counter-rolling movement of the balloon component toward the pylorus.

FIG. 1b schematically shows how the duodenal shoulder 6z of the balloon 6 presses in axially-oriented counter-rolling (arrow D) against the duodenal shoulder surface of the pylorus P. The force acting in total from the duodenal side Z and from the gastric side M on the pylorus can be adjusted by the user by way of the respective filling pressure in the balloon element 6 and adapted as needed in the individual in the course of the application. In contrast to known duodenal bypass devices, the contact pressing mechanism, which is ensured by the axially elastic rolling movement in the direction B toward the pylorus (arrow D) and in the opposite direction E away from the pylorus (arrow E), dynamically follows the respective functional state of the sphincter. Functional variations of the width of the sphincter and/or the length of the pylorus channel are thus progressively compensated for and therefore an optimum motility-compatible seal of the fixing unit in the pylorus is enabled.

In the devices described in FIGS. 1 and 1a to 1c, the gastric buttress element 5 can be embodied as a soft, elastically deformable, for example, gel-type structure. Alternatively, a balloon body applied in a conventional manner, i.e., without inverted fixation of the balloon ends and without corresponding counter-rolling effect, can also be used as a gastric buttress element.

The conducting element 4 can be embodied as a relatively rigid, tubular element, but preferably has the capability of elastic radial unfolding and self-erection. The lumen of the conducting element which respectively results in the sphincter is preferably to follow the physiological sphincter closure with the least possible counteracting elastic resistance. At maximum sphincter tonus, the conducting element is intended to deform to a nearly leak-tight closed residual lumen, following the complete contraction travel of the sphincter.

The described elastically acting radially folding/eversion of the conducting element passing the sphincter is preferably ensured by a tube material having primary elastic properties, for example, polyurethane (PUR). For example, PUR types of the variety Elastollan 1180A and 1185A, from BASF, have a corresponding elasticity when they are formed into a tube body having a diameter of approximately 20 mm and a tube wall thickness of approximately 200 μm.

Figure 1C:
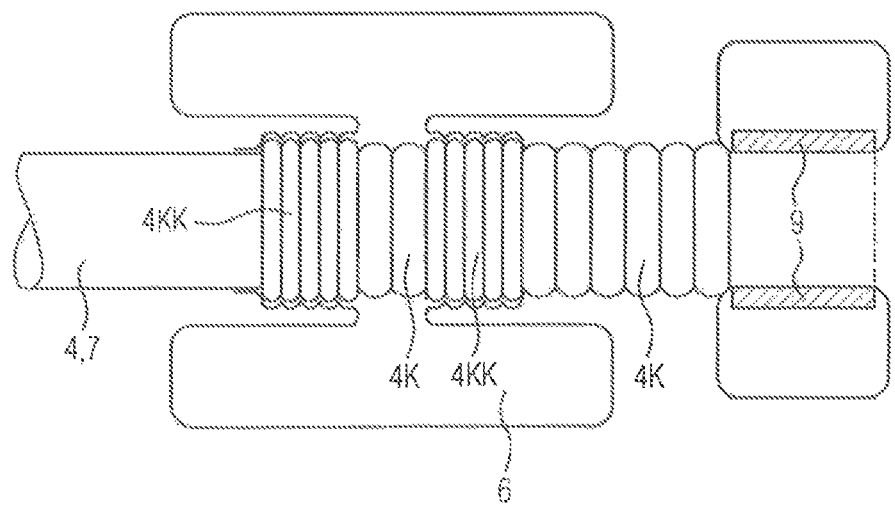
FIG. 1c shows a corrugated tube-like corrugated embodiment of the transpyloric conducting element placed in the pylorus.

The elastic folding capability or elastically acting erection of the tube body can be improved in its effectiveness by a corrugated tube-like profile of the conducting element. Such a profile additionally enables a reduction of the tube wall thickness. Thus, for example, as shown in FIG. 1c, a conducting element 4 as a continuous tube body can be provided with an annular or spiral corrugated profile 4k or also 4kk, wherein the tube body preferably consists of Elastollan of the variety 1180A, has an inner diameter of approximately 20 mm, a wall thickness of approximately 150 to 200 μm, the corrugation has an amplitude of 1 to 2 mm (preferably 1.5 mm), and a peak-to-peak distance of 1 to 2.5 mm (preferably 1.5 to 2 mm). For further modification of its elastic properties, the corrugated profile can additionally be coated in individual segments with an additional, for example, gel-type material layer, which modifies the folding mechanism.

The structural design of the terminal segments 4a and 4b of the conducting element, which accept balloon or buttress bodies in a supporting manner on the outer side thereof, is of particular significance for the function of the device. The segments are preferably designed such that they elastically unfold upon a certain force action and accordingly elastically erect themselves upon decreasing force. In principle, upon the development of an elastically self-erecting effect of the terminal segments 4a and 4b, the same design elements which modify the deformation and erection properties, can be used as described above in the construction of the transpyloric segment.

Because the forces acting radially on the terminal segments 4a and 4b are generally greater than the forces acting on the transpyloric segment, the elastic, lumen-erecting effect thereof should accordingly be strengthened, for example, by a particularly tight corrugation 4kk (peak-topeak distance of less than 1.5 mm, for example) or by annular elements 9 which reinforce the conducting element. The elastic action of the terminal segments should be dimensioned such that they withstand an externally loading filling pressure of 20 to 100 mbar, preferably 20 to 60 mbar, without collapse of the lumen. A rigid-walled, non-collapsible embodiment of the segments 4a and 4b is conceivable within the scope of the invention, but is disadvantageous for the function.

Figure 2:
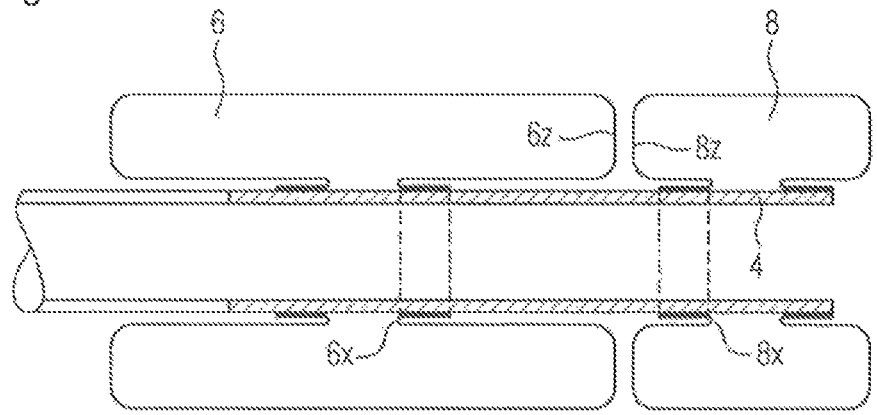
FIG. 2 shows an embodiment having balloon components arranged on both sides, which roll axially toward the pylorus.
Figure 2A:
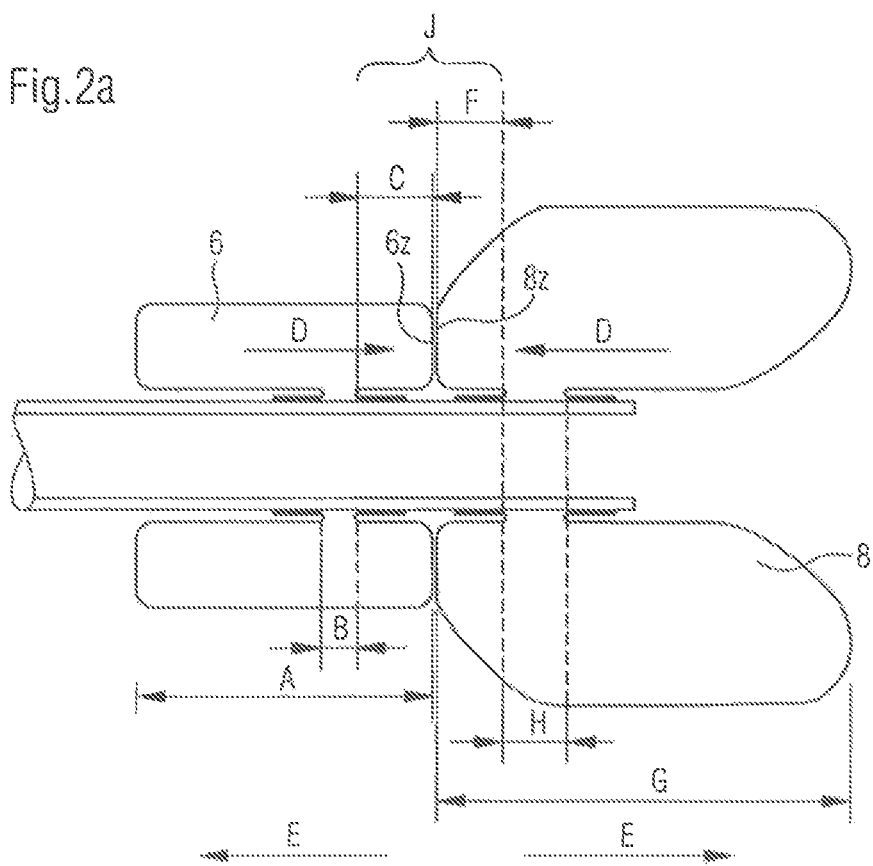
FIG. 2a shows an embodiment corresponding to FIG. 2 having back-rolling balloon components on both sides, wherein the gastric balloon is enlarged in a space-occupying manner.

FIGS. 2 and 2a show the device according to the invention with two terminal balloon elements, which are arranged on the conducting element 4 and are each capable of back-rolling or counter-rolling, wherein the formation geometry, the balloon materials, and the specifically inverted mounting of the balloons on the conducting element correspond to the guidelines of the above figures in the case of both balloon elements. In the preferred embodiment, the two balloons positioned opposite to one another are connected by a communicated filling line, identical pressures thus result in both compartments upon the filling of the device.

The preferably cylindrical balloon bodies 6 and 8, which are each formed with steep shoulders, are to be placed in this case on the conducting element 4 such that the respective shoulder surfaces 6z and 8z, upon free filling of the balloons, outside the body, in the respective neutral position thereof or without deflection from the neutral position thereof, face one another at a free distance of not greater than 5 mm, i.e., the assumed width of the pylorus. In this case, the distance J between the terminus edges 6x and 8x, which is decisive for the mounting of the balloon bodies, corresponds to the total of (A/2–B/2)+(G/2–H/2)+5 mm. In the filled state of the balloon bodies 6 and 8, the shoulder surfaces 6z and 8z then load the pylorus in situ nearly without contact pressure. In the preferred embodiment variant of the device, the mounting-relevant distance J is less than the total of (A/2–B/2)+(G/2–H/2)+5 mm, however, and particularly preferably less than the total of (A/2–B/2)+(G/2–H/2). The "rolling paths" resulting upon filling of the balloon body from the counteracting forces correspond to the distances C<(A/2–B/2) and F<(G/2–H/2). Upon free filling of the balloon bodies, contact of the shoulder surfaces 6z and 8z occurs in this case, even before the neutral location of the balloon bodies is reached, the shoulder surfaces then press against one another, depending on the respective filling pressure. In the optimum case, the mounting-relevant distance J corresponds to the total of (A/2–B/2) and (G/2–H/2)–5 to –10 mm. With such a shortening of the distance J, independently of the respective contraction state of the pylorus, an elastic deflection of the balloon bodies results on both sides in the direction E, as well as a correspondingly acting, contact-pressure rolling movement D of the shoulder surfaces. If functional changes of the width of the pyloric sphincter occur, they can be compensated for by the described elasticity and counter-rolling, with substantially maintained anchoring and sealing-action tension above the pylorus.

The radial diameter of the gastric balloon body 8 can preferably be enlarged such that it fills the region of the gastric antrum, which adjoins the pylorus on the gastric side, in a space-occupying manner, and/or puts the wall thereof under a moderate tension, thereby conveying to the patient a feeling of fullness. The side of the balloon body 8 facing toward the stomach is preferably embodied as a funnel-shaped orifice T. The funnel shape of the "mouthpiece" accepting the chyme can be stabilized in its shape and action by a self-erecting, stent-like framework, which is installed in the mouthpiece region.

Figure 3:
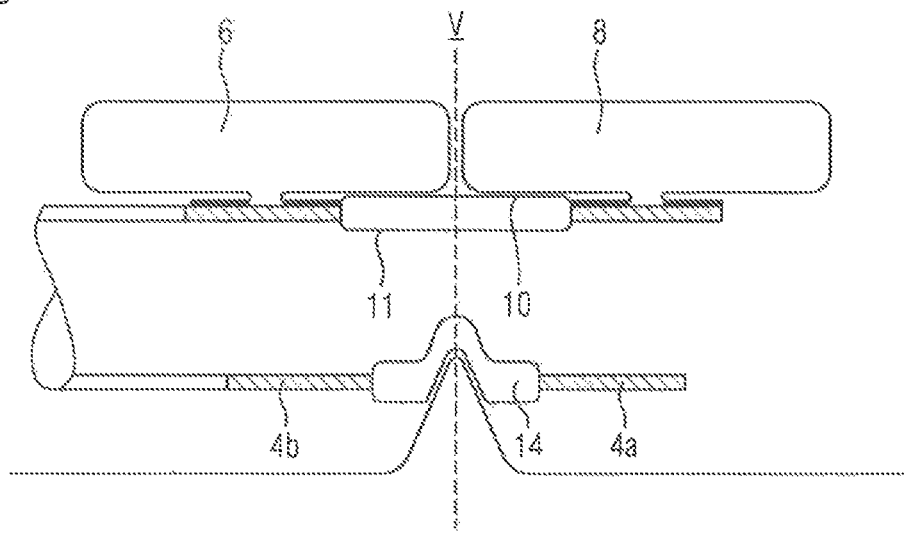
FIG. 3 shows an embodiment of the invention having back-rolling balloon components arranged on both sides, in conjunction with a concentric double-layered, film-based transpyloric conducting element.
Figure 3A:
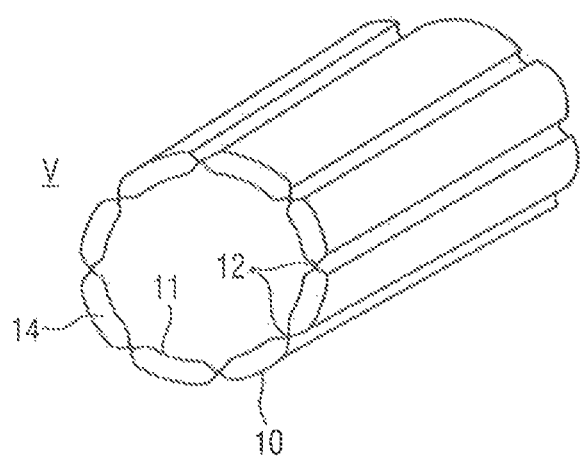
FIG. 3a shows the web-like connection of the concentric film layers in the region of the transpyloric conduction.

FIG. 3 shows an embodiment of the bypass device, in which the transpyloric section of the conducting element 14 consists of a concentric double-layered arrangement of tube films 10 and 11, which are fixedly connected to one another by, for example, axially longitudinally-extending welding lines 12 or also by uniformly distributed punctiform spot welds. For this purpose, see the sectional plane V through the conducting element 14, which is shown in FIG. 3a. The concentric tube films of the conducting element thus form a cylindrical, fillable hollow tube 14. Upon filling of or application of pressure to the hollow tube, which is "quilted" like an air mattress in the described manner, the quasi-air-stabilized tubular body erects itself radially in circular form. In addition to the radial erection, axial untwisting over the longitudinal axis additionally occurs. The hollow tube 14 is connected to one or preferably to both balloon segments 6 and 8 in a volume-communicating manner and is preferably filled via a shared filling device. It is advantageous for the particular tissue or organ compatibility that the lumen-erecting effect in the transpyloric segment of the device can be overcome relatively easily by the pyloric sphincter, i.e., the sphincter can move relatively freely. In spite of a continuous axial contact pressure of the balloon segments 6 and 8 against the shoulder surfaces of the pylorus, it is hardly impaired in its capability to contract. If a contraction of the gastric antrum occurs in the scope of reflexive gastric emptying, it is absorbed by the gastric balloon element and causes a corresponding pressure increase for the duration of the pressure decrease in the compartments connected thereto. The transient pressure increase in turn results in an intensification of the axial counter-rolling of the balloon segments, whereby the tubular hose 14 connecting the two segments is tightened over its longitudinal axis and therefore the opening and untwisting of the lumen is assisted.

The concentric tube films 10 and 11 preferably consists of PUR, for example, in the hardness range of Shore 80 A to 60 D, preferably in the range of 90 A to 55 D. The wall thickness of the films should be approximately 15 to 50 µm, preferably 20 to 30 µm. For example, PUR of the family Pellethane 2363 from Lubrizol Inc. can be used as the material type.

Figure 3B:
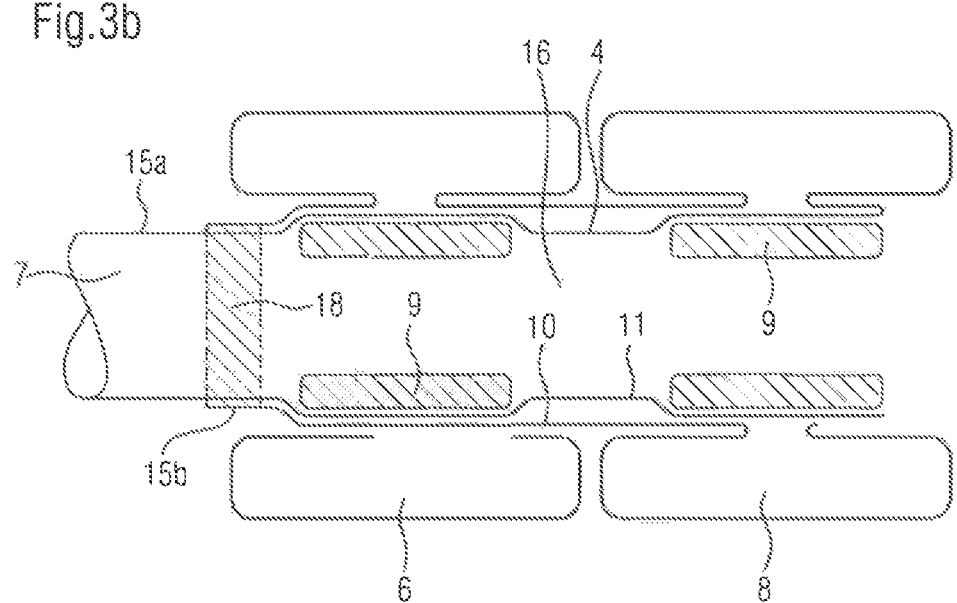
FIG. 3b shows an embodiment as in FIG. 3, wherein the lumen-stabilizing sleeve elements are arranged in the inner lumen of the conducting channel, however.

FIG. 3b shows a further preferred embodiment of the device type having a pneumatically self-erecting, coaxially constructed tubular hose. All compartment-forming components of the device, i.e., both the two balloon segments 6 and 8 and also the interposed conducting segment, consist here of a single balloon film, which is a continuously formed body that is subsequently everted. It is already provided during the production with all functionally and structurally required formations and molded to its complete operating dimensions. The end 15a of the formed balloon film is everted by the opposing balloon body end 15b such that the various balloon segments are represented in configuration with the elements of the conducting element in the manner shown. The central openings of the terminal balloon segments 6 and 8 are each stabilized by elastically erecting sleeve elements 9, which are inserted into the conducting lumen 16 of the head unit. The sleeve elements are used to accept and fix the terminal balloon segments, wherein preferably the instructions described in FIGS. 1 and 2 apply, and therefore an axial rolling movement of the terminal balloon segments, which is oriented toward the pylorus, is ensured. The two film layers 10 and 11 extend completely from the inverted balloon body in this embodiment. The end 15a of the formed balloon body can additionally be lengthened in that the transduodenal bypass tube 7 protrudes therefrom without a required joint.

Figure 3C:
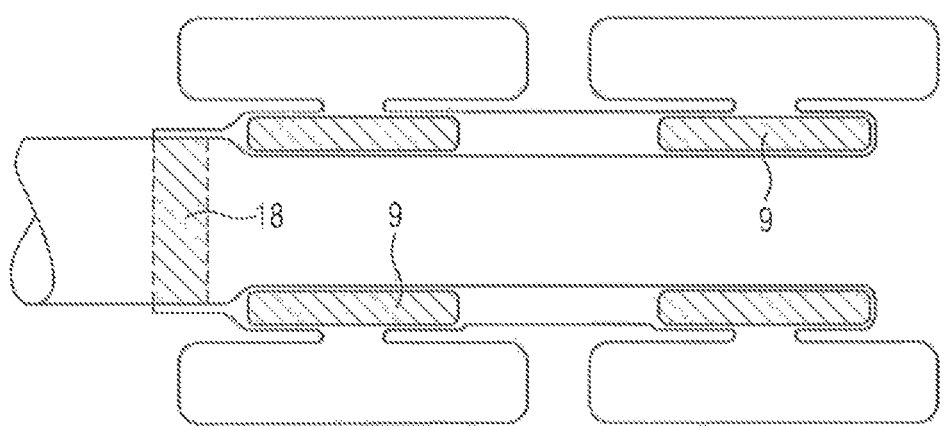
FIG. 3c shows an embodiment in FIG. 3, wherein the lumen-stabilizing sleeve elements are arranged in the interior of an everted balloon element.

FIG. 3c shows a corresponding embodiment, in which the lumen-stabilizing sleeve elements 9 are not arranged in the conducting lumen 16, but rather are installed in the interior of the everted balloon body.

Figure 4:
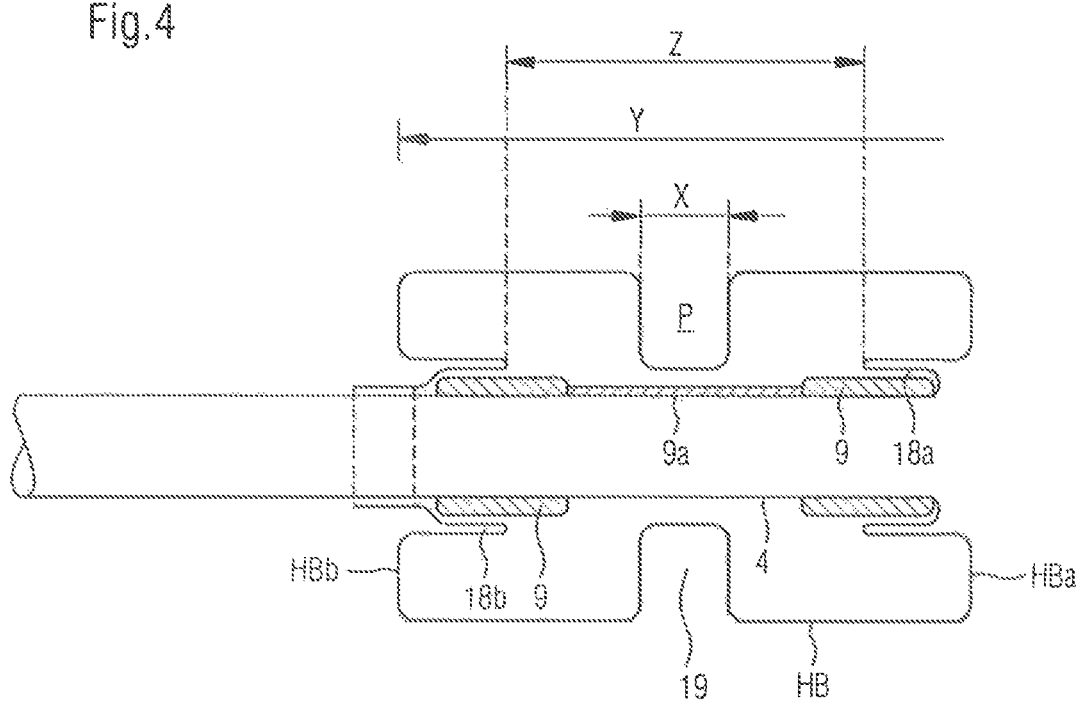
FIG. 4 shows an embodiment having a continuously formed balloon body tapered in a dumbbell shape in the region of the transpyloric component.

FIG. 4 shows a further embodiment of the device, in which all segments of the head unit extend from a completely formed, completely everted, dumbbell-shaped balloon body HB, wherein the terminal balloon segments HBa and HBb are applied with the balloon ends 18a and 18b to the supporting sleeve elements 9 or the conducting element 4. The balloon body HB has no further connection to the balloon-supporting conducting element beyond the balloon ends 18a and 18b. The central section of the balloon body is provided during the molding with a constriction 19 to accept the pyloric sphincter. The distance X (distance between the shoulder faces of the constriction) is not to exceed (Y−Z)/2. The opposing shoulder faces of the balloon segments HBa and HBb move toward one another during the filling of the balloon in the illustrated embodiment and cling radially and axially to form a seal to the sphincter seated in the constriction. With increasing filling pressure of the balloon HB, the intensity of the pressing and sealing action oriented toward the pylorus increases accordingly.

The conducting element 4 consists in the present embodiment of a continuously formed tube element, which forms both the terminal elements 9 for accepting the ends of the balloon body and also the interposed element 9a, which is exposed to the sphincter. The above-described deformability of the element 9a during the sphincter contraction and the spontaneous elastic direction after deformation is taken into consideration in this embodiment of the device.

Figure 5:
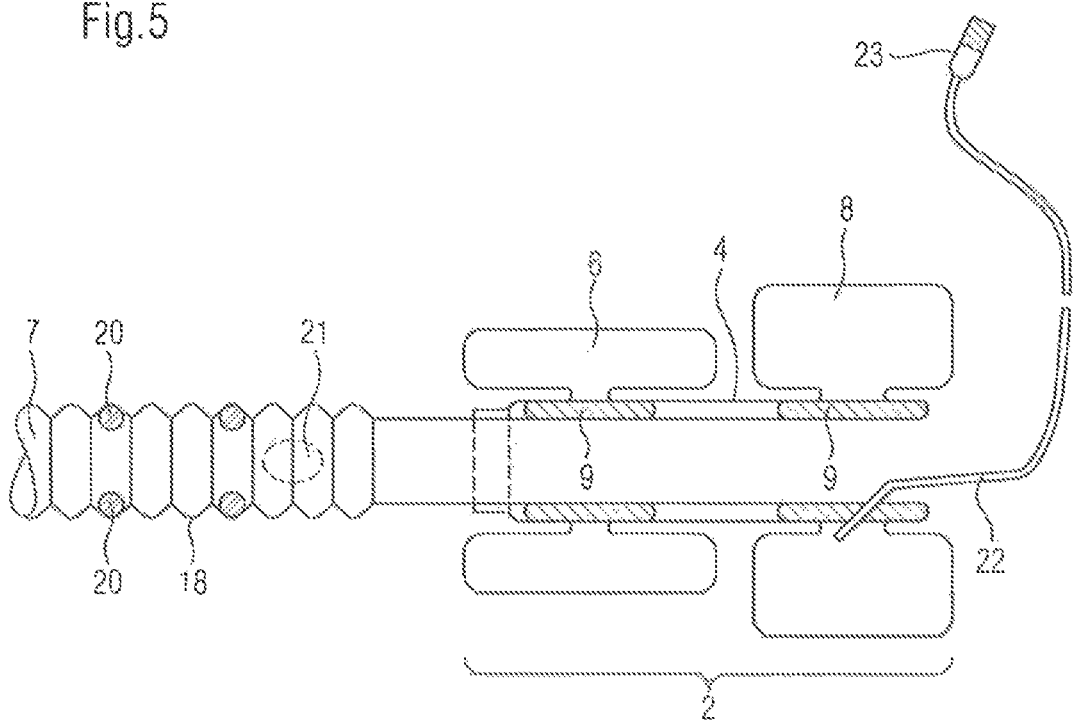
FIG. 5 shows an embodiment having back-rolling balloon components attached on both sides, transduodenal extension tube, and intra-gastric space-occupying balloon element.

FIG. 5 shows the structure of a device according to the invention according to FIG. 3a in an overview, consisting of the following functional units: transpyloric fixing device 2 (consisting of: gastric 8 and duodenal 6 balloon elements with supporting sleeve elements 9, conducting element 4), and transduodenal bypass element 7.

The duodenal bypass element 7 preferably has a wall thickness of 10 to 80 µm, preferably 15 to 30 µm, preferably consists of the same material as the functional units of the fixing device to which medium is applied, and is preferably provided with a lumen-erecting, annular or spiral corrugated profile 18. In addition to the radial erection of the lumen, the corrugation is to assist the spontaneous axial untwisting of the tube. The length of the tube is preferably dimensioned such that the aboral end extends up into the terminal duodenum or also into the beginning jejunum. To modify the bypass effect, the element 7 can also be provided with openings 20, which enable the partial passage of food into higher regions of the duodenum.

The dimensioning of the transpyloric fixing device is preferably implemented as follows: duodenal balloon element 6 (cylindrical diameter 25 to 35 mm; cylindrical length 15 to 50 mm, preferably 20 to 30 mm), gastric balloon segment 8 (cylindrical diameter 50 to 80 mm, cylindrical length 30 to 100 mm, preferably 40 to 60 mm), transpyloric segment 4 (diameter 15 to 30 mm, preferably 20 to 25 mm; length 5 to 15 mm, preferably 8 to 12 mm).

The compartments of the device which are fillable or to which pressure can be applied are preferably connected to one another in a communicating manner. The filling is performed, for example, by a filling tube 22, which opens into the region of the gastric balloon segment and which is designed in its length so that it slides out orally and can be filled and/or its filling can be readjusted via its terminal closure 23 outside the body.

Figure 6A:
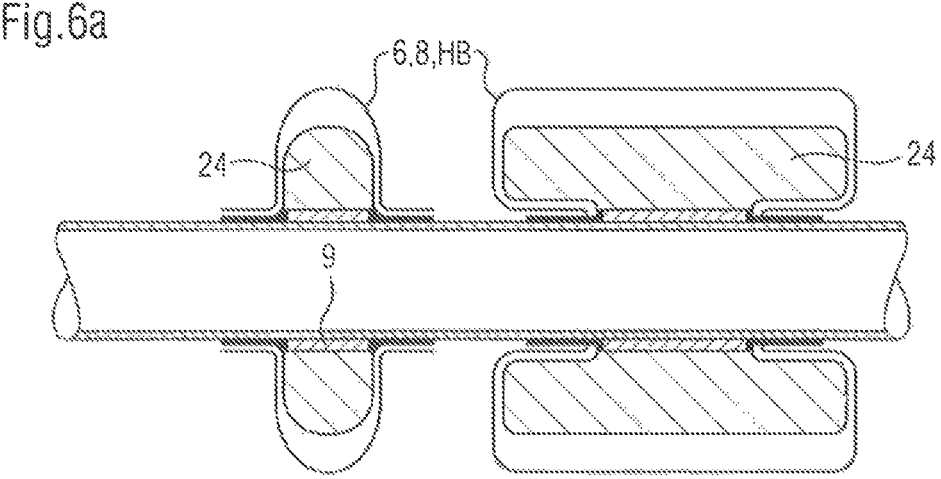
FIGS. 6a and 6b show embodiments having a balloon-in-balloon configuration and separated filling in each case using compressible and non-compressible media.
Figure 6B:
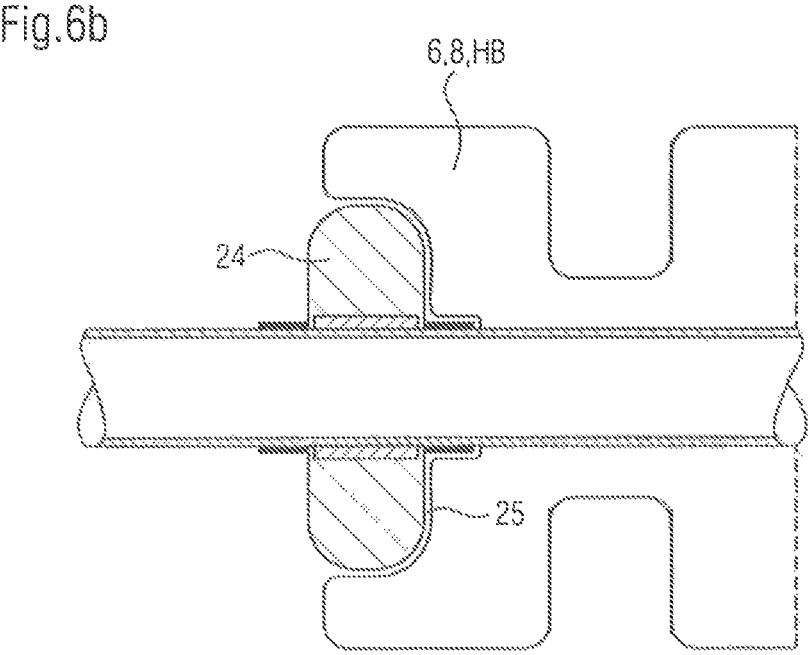

FIGS. 6a and 6b describe further embodiments of the above-described construction types, in which, in particular to improve the transpyloric anchoring, an additional anchor balloon element 24 is arranged inside a balloon element or a balloon-like expanded segment, for example, 6, 8, or also HB. This balloon element is filled by a separate supply line. For this purpose, a medium can be used which qualitatively differs from the filling medium of the region surrounding it. The anchor balloon element is completely enclosed by the surrounding balloon in a preferred embodiment. The anchor balloon element 24 can optionally be used on both sides of the pylorus. It preferably consists of material which has the characteristics of a soft film, but does not substantially exceed a predetermined shape and/or dimension upon filling and therefore precludes uncontrolled elastic expansion. If the duodenal anchoring of the device is paramount as the functional purpose, a discoid form is preferably selected. If counter-rolling oriented toward the pylorus is additionally desired, a cylindrical structural form can be used, wherein the mounting guidelines described according to the invention, which generate the counter-rolling, are applied. The element 24 is preferably filled with a non-compressible medium, for example, water or oil, while the surrounding balloon element preferably contains a gaseous medium.

Alternatively to a complete housing of the balloon 24 in a surrounding balloon, the balloon 24 can also be enclosed only in portions, as shown in FIG. 6b, by the surrounding balloon. The contact surface 25 between the two balloon envelopes can be fixedly connected or also unconnected. In a less preferred combination of a balloon element 24 having a primarily anchoring effect with a balloon element 6, 8, or HB having a primarily sealing effect, a sequential arrangement of the balloon elements on the shaft element is also conceivable.

Figure 7A:
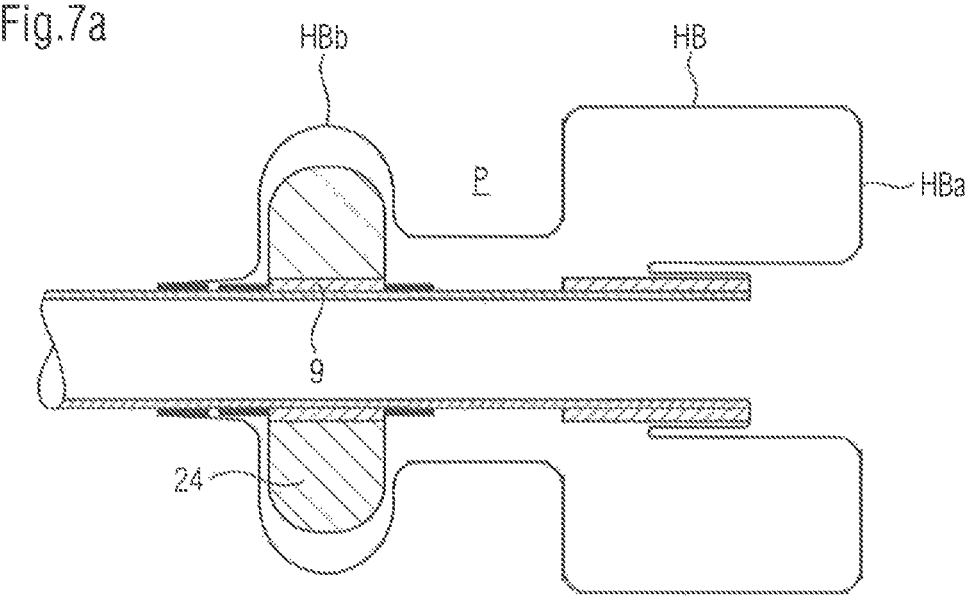
FIGS. 7a and 7b show preferred embodiments having a continuous, dumbbell-shaped, transpyloric sealing balloon and a duodenal additional fixing balloon which is partially or completely enclosed by the sealing balloon.
Figure 7B:
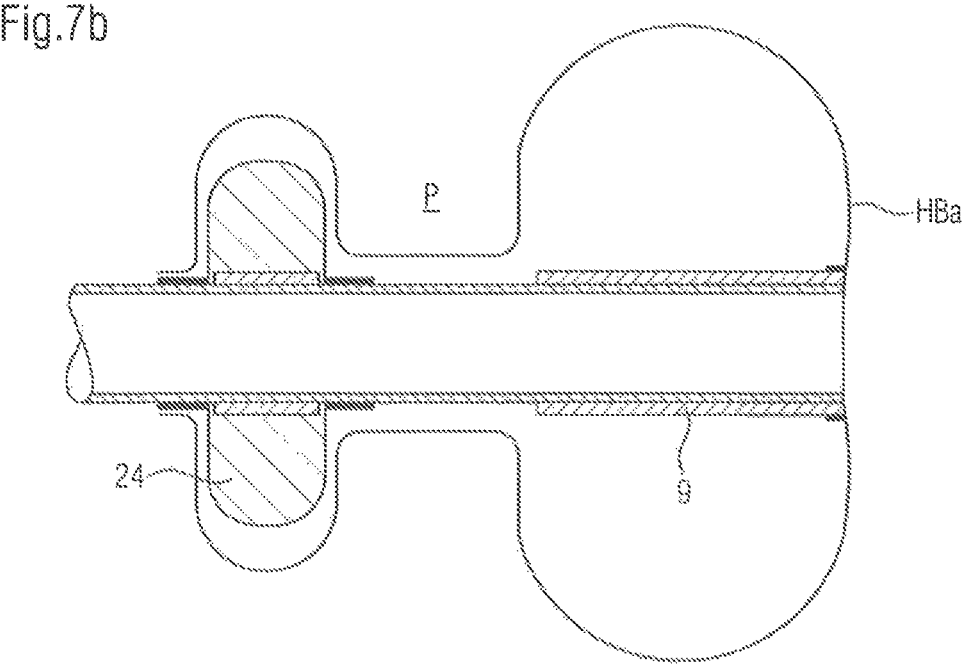

FIGS. 7a and 7b show a preferred embodiment of the device based on the construction types described in FIG. 4 and FIG. 6, in which the conducting element 4 carries a dumbbell-shaped balloon HB, which is mounted on the conducting element thus resulting in the counter-rolling of the terminal balloon segments HBa and HBb, which is oriented toward the pylorus P, and which is described in FIG. 4. The additional balloon element 24 is only installed on the duodenal side in the presented embodiment and has a discoid shape. The contour of the balloon 24 preferably corresponds to the contour of the duodenal balloon segment HBb enveloping the balloon. The balloon HBb should exceed the diameter dimensions of the inner balloon 24, while its axial length corresponds to that of the balloon 24 in a preferred embodiment. The balloon 24 is placed directly behind the pylorus in the duodenal bulb. The counter-rolling of the gastric balloon segment HBa toward the pylorus is achieved, similarly to the construction described in FIG. 4, by an inversion of the balloon end of the balloon segment HBa. During the transpyloric application of the described embodiment, initially the element 24 is filled with liquid and the device is thus secured in its position on the duodenal side. Subsequently, an air filling is applied to the surrounding balloon, whereby it both clings to the exposed mucosa to form a radial seal and also presses axially against the shoulder faces of the pylorus. The surrounding balloon thus assumes, in addition to the effect as a gastric buttress or as a space-occupying body in the gastric antrum, a predominantly sealing function. Its wall thickness is preferably in the range of 10 to 30 µm, less preferably in the range of 30 to 100 µm. The material hardness should be in the range of Shore 80 A to 75 D, but preferably 85 A to 65 D. The special combination of thin walls and material hardness of the surrounding dumbbell shape balloon HB enables it to absorb forces prevailing on the gastric side over a large area and to use them for efficient sealing from stomach contents in the region of the pyloric passage and in the duodenal section of the balloon body. If a contraction of the gastric antrum occurs, the contraction force is absorbed on the gastric side and filling volume, with corresponding increase of the filling pressure, is displaced into the corresponding balloon portions. The described material hardness limits the elongation of the balloon envelope in this case and therefore prevents the partial emptying of one balloon portion into an adjoining balloon portion. The particularly thin-walled nature of the balloon envelope HB enables all segments of the balloon body to be dimensioned residually, which corresponds to a formation of the respective segments beyond the anatomical dimensions which are required or to be assumed. The residually formed balloon body then presses against the mucosal surfaces as the balloon envelope unfolds, wherein a sealing closure is nonetheless ensured. With corresponding volume displacement from the gastric portion into the pyloric and duodenal portion, enabled by the residual excess, a force-absorbing elastic expansion of the envelope can thus be avoided, and the respective force acting on the gastric side can be used in its entirety for the pyloric and duodenal seal. In the design of the conducting element 4 and/or the sleeve elements 9, the elastic self-erection action thereof has to be designed so that in the event of a transient, contraction-related pressure increase within the balloon HB, a collapse of the conducting lumen 16 can be avoided.

FIG. 7b shows a similar embodiment, in which the counter-rolling of the gastric balloon segment HBa is nearly completely or completely omitted and only a radially acting seal of the enclosing balloon envelope acts in relation to the pylorus. The inversion of the gastric shaft ends of the balloon envelope HB described in FIG. 7a is not applied here.

Figure 8:
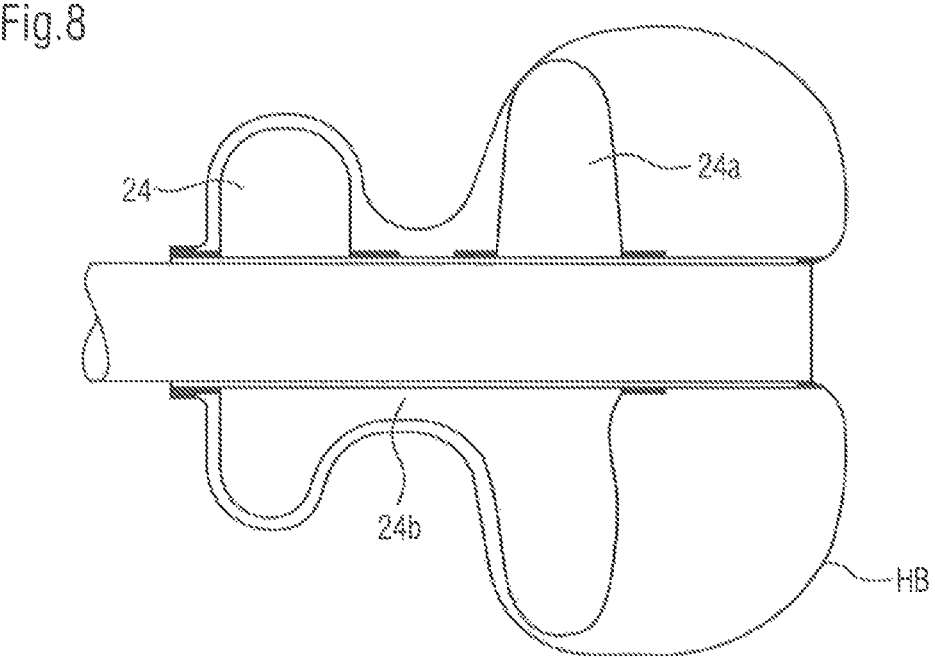
FIG. 8 shows an embodiment based on FIG. 7b, wherein the additional fixing element is arranged on both sides of the pylorus.

FIG. 8 shows an embodiment variant based on FIG. 7b, in which an anchoring balloon element 24 is placed not only on the duodenal side, but also on the gastric side. The gastric element 24a also has a discoid shape in the preferred embodiment and can be adapted in radial dimensions to the space conditions of the gastric antrum. Both elements 24 and 24a can be fillable separately or alternatively a medium can be applied thereto via a shared supply line. Furthermore, both elements can be connected to one another by a dumbbell-shaped constriction 24b, which is placed in the pyloric passage. A polyurethane of low compliance is preferably also used for the embodiment of the elements 24 and 24a, to avoid volume shifting into communicating compartments upon loading of a balloon compartment and resulting in an undesired elastic elongation of the balloon envelope. The illustrated variant having flanking of the pylorus on both sides with an anchoring balloon element 24 enables an additional securing function, if the balloon envelope HB housing the balloon elements 24 is damaged and loses its filling. The transpyloric placement of the device remains ensured due to the bilateral arrangement of the elements 24.

Figure 9A:
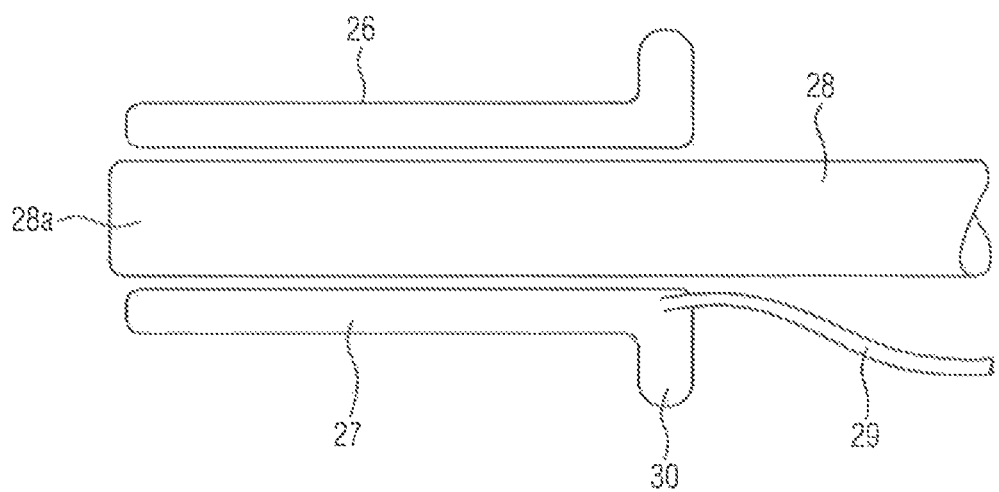
FIG. 9a discloses a simple embodiment of a transport, and/or fixing or dropping device, for the application of the device to the outside hull of e.g. an endoscope.

FIG. 9a shows an exemplary embodiment of a dropping mechanism or applicator 26, which is required for an endoscopic application and is embodied as a cylindrical coupling balloon 27 and is drawn onto the shaft 28 of an endoscope or catheter. Positioned on the terminal end 28a of the endoscope or catheter, or within a distance of about 5 to 15 cm from the distal end of the endoscope or catheter, it presses against the channel wall of the conducting segment 4 of the bypass head unit upon filling and thus establishes the coupling between bypass and endoscope. If the filling is removed from the balloon 27, the coupling disengages, and the endoscope shaft can be retracted from the channel of the head unit or also advanced in the duodenal direction. The balloon is filled from outside the body through a supply line 29.

To ensure secure positioning of the bypass on the dropping mechanism or applicator, the coupling balloon 27 can be provided with a proximal, shoulder-type formation 30, which serves as a mechanically active stop. A corresponding stop function can also be integrated, independently of a continuous cylindrically-embodied coupling balloon, as a separately unfolding buttress balloon in the proximal end of the coupling unit. A corresponding formation or a corresponding separate buttress balloon can additionally also be formed or arranged distal to the bypass. The coupling balloon 27 therefore assumes a dumbbell shape, which accepts the bypass device in the tapered region in a supporting manner. The envelope of the coupling balloon is preferably formed from a PUR-based material of low compliance, especially with a Shore hardness between 60 A to 95 A, especially between 70 A and 90 A, and a liquid, non-compressible medium is preferably applied thereto.

Figure 9B:
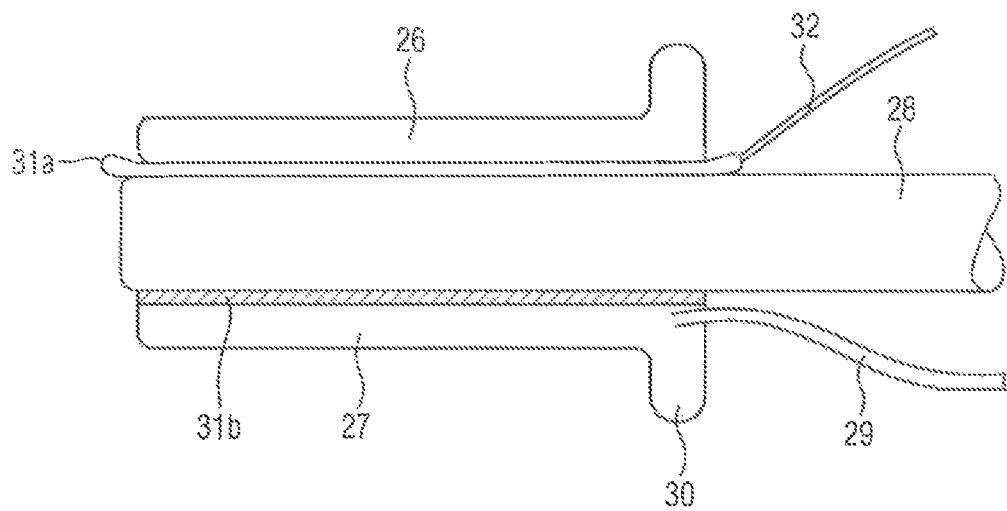
FIG. 9b shows another embodiment of a of a transport, and/or fixing or dropping device corresponding to FIG. 9a, comprising an additional function, avoiding axial dislocation of the unit on the endoscope or catheter shaft.

FIG. 9b shows a similar embodiment to FIG. 9a, whereby the cylindrical coupling balloon 27 is equipped on the inside of its cylindrical channel with an additional component 31a or material layer 31b, securing a secure positioning of the coupling unit on the endoscope or catheter shaft, preventing any axial dislocation. The fixing function can be effected by a cylindrical balloon element 31a, which can be inflated from outside of the body by a filling line 32. The balloon element 31a is preferably made from a low-compliant material, reliably limiting radial extension of the balloon, avoiding that the balloon in the filled state is causing a coupling effect of the unit to the inside surface of the trans-pyloric bypass segment. The balloon element 31a is fixed to the coupling balloon 27 preferably by an adhesive or solvent bonding.

The axial position can be further secured by a cylindrical layer of elastically expanding material 31b, which is connected to the inner channel of the coupling balloon in a fixed fashion, resting on the endoscope or catheter shaft under sufficient elastic stretch, effecting a dislocation preventing grip of the unit.

The endoscopic placement of a bypass device according to FIG. 7a or 7b is described hereafter by way of example.

If the bypass device seated on the endoscope tip has reached the stomach interior, firstly the outer dumbbell-shaped balloon HB is filled, preferably with 60 to 80% of its free unfolded volume. The balloon HB, which is thus filled with air in a tension-free manner, is now inserted using the endoscope into the pylorus until the pyloric shoulder of the gastric balloon segment HBa stops on the pylorus and prevents a further endoscopic advance of the bypass. The resistance resulting upon the stop of the balloon shoulder in the gastric outlet region is perceived by the user and confirms the correct transpyloric placement of the device. The internal anchor balloon 24 is then filled with a liquid medium. The outer balloon HB is subsequently filled up to its final operating dimensions.

If the head unit of the bypass device is thus secured in its transpyloric position, the bypass is released from the applicator or endoscope shaft by emptying the coupling balloon 27 and the applicator or endoscope tip is inserted further into the duodenum. In this case, the duodenal conducting portion 7 of the bypass device can be grasped using a corresponding instrument on the applicator or endoscope tip and transported into the duodenum. The device provides a suitable extension on the lower free end of the transduodenal tube 7 for this purpose. If the respective possible duodenal insertion depth of the applicator or endoscope shaft is reached, the free lower tube end of the bypass can be conveyed further into the duodenum by advancing the gripping instrument and finally dropped therein.

If the transduodenal conducting portion 7 of the device is thus partially or completely unfolded, an air insufflation into the tube or also flushing with fluid can take place for further lumen-opening unfolding of the portion 7. This is preferably performed in such a way that the coupling balloon 27 seated on the applicator or endoscope shaft is placed in the lumen of the head unit and is blocked to form a seal therein for the duration of the insufflation or flushing, respectively. Therefore, the lumen-erecting and lumen-aligning filling of the duodenal tube portion 7 can also take place without any reflux into the stomach.

When removing the device from its trans-pyloric position, a coupling unit or applicator, as described in FIGS. 9a and 9b is positioned on the tip portion of an endoscope or catheter device with similar functionalities to an endoscope. Once inserted into the stomach of the patient, the coupling balloon 27 is filled with a certain inflation volume, preferably of a fluid, whereby the filling volume of the balloon does not effect a mechanical grip between the two units, but is sufficient to unfold and circularly erect the proximal balloon extension 30, when being inserted into the central lumen of the head-unit, which are then performing as a mechanical bolster, limiting the insertion depth of the endoscope or catheter into the bypass device. Once the balloon extension 30 is colliding with the entry portion of the head unit, the coupling balloon 27 is filled to its working state, effecting a tight grip to the bypass, allowing for removal of the deflated device from its pyloric position and for retraction through the esophagus and the pharynx of the patient.

LIST OF REFERENCE SIGNS 1 bypass device
2 fixing unit
4 conducting element
4a gastric end
4b duodenal end
4kk corrugation
5 buttress element
5z gastric shoulder
6 duodenal balloon element
6x terminus edge
6y terminus edge
6z pyloric shoulder
7 tube element
8 gastric balloon element
8z shoulder
9 element, sleeve element
10 tube film
11 tube film
12 weld line
14 conducting element
15a end
15b end
16 lumen
18 corrugated profile
18a balloon end
18b balloon end
19 constriction
20 opening
22 filling tube
23 terminal closure
24 anchor balloon element
24a gastric element
24b constriction
25 contact surface
26 dropping mechanism
27 coupling balloon
28 shaft
29 supply line
A cylindrical contact surface
B distance
C distance
D rolling movement, arrow
E opposite direction, arrow
HB dumbbell-shaped balloon body
HBa balloon segment
HBb balloon segment
J distance
M gastric side
P pylorus
T orifice
X distance
Z duodenal side

The invention claimed is:

1. A method for the application of a transpyloric and, if applicable, transduodenal bypass device (1) for accepting chyme from the stomach and for bypass-type conducting of the chyme through the pylorus in or through the duodenum of a patient, comprising a tubular, preferably radially collapsible and self-erecting transpyloric conducting element (4,7), which penetrates the pylorus, having a central conducting lumen for the chyme, wherein the bypass device comprises fixing elements for anchoring the transpyloric conducting element (4,7) on the pylorus, comprising an annular gastric anchor element, which is arranged on the gastric side or proximal to the pylorus, for anchoring the transpyloric conducting element (4,7) proximally to the pylorus, having a gastric balloon segment (8), which regionally delimits a cavity of annular structure fillable with a medium, and also comprising an annular duodenal anchor element, which is located on the intestine side or distally to the pylorus in the duodenum, for anchoring the transpyloric conducting element (4,7) distally to the pylorus, having a duodenal balloon segment (6), which regionally delimits a cavity of annular structure fillable with a medium, by use of an applicator, comprising the following steps:
 a) sliding or plugging the applicator (26) onto the shaft (28) of the endoscope or catheter;
 b) placing or plugging the bypass device (1) on the applicator (26), so that it penetrates the central conducting lumen of the transpyloric conducting element (4,7) of the bypass device (1);
 c) fixing the bypass device (1) by activating a fixation mechanism, especially by filling a gap-bridging balloon between the applicator (28) and the inner side of the conducting lumen of the transpyloric conducting element (4,7) of the bypass device (1);
 d) inserting the bypass device (1) by means of the endoscope or catheter into the stomach of a patient in an antegrade way through the upper digestive tract;
 e) partially or completely filling the gastric balloon segment (8) of the gastric anchor element;
 f) inserting the distal section of the conducting element (4, 7) through the pylorus, until the entirely or partially filled gastric balloon segment rests proximal to the pylorus and noticeably resists a further advance of the bypass device (1);

g) filling the duodenal balloon segment (6) to anchor the duodenal anchor element distal to the pylorus;
h) releasing the distal section of the conducting element (4, 7); and
i) detaching the bypass device (1) by deactivating the fixation mechanism, especially by deaerating the gap-bridging balloon between applicator shaft and inner side of the conducting lumen.

2. The method according to claim 1, characterized in that, between steps h) and i), liquid is flushed extracorporeally into the duodenum via flushing openings arranged distal to the gap-bridging balloon on the applicator shaft, to unfold the distal section of the conducting element (4,7).

3. The method according to claim 1, characterized in that each lumen of the filling lines is closed by a valve or by a valve-like decoupling mechanism, when the filling lines are mechanically disconnected from the trans-pylorically positioned bypass.

4. The method according to claim 1, characterized in that, after step i), the lumina of the filling lines are permanently occluded by thermal welding of the tubing or by filling of the tubing with a lumen occluding, spontaneously curing adhesive/substance.

5. The method according to claim 1, characterized in that, after step i), the supply lines of the balloon segments (6, 8), especially the closed or occluded supply lines of the balloon segments (6, 8), are dropped into the stomach and remain therein until the bypass device (1) is removed.

* * * * *